(12) United States Patent
Binmoeller

(10) Patent No.: US 9,352,126 B2
(45) Date of Patent: May 31, 2016

(54) METHODS AND DEVICES TO CURB APPETITE AND/OR REDUCE FOOD INTAKE

(71) Applicant: Endosphere, Inc., Columbus, OH (US)

(72) Inventor: Kenneth F. Binmoeller, Rancho Santa Fe, CA (US)

(73) Assignee: Endosphere, Inc., Columbus, OH (US)

( * ) Notice: Subject to any disclaimer, the term of this patent is extended or adjusted under 35 U.S.C. 154(b) by 0 days.

(21) Appl. No.: 13/768,659

(22) Filed: Feb. 15, 2013

(65) Prior Publication Data

US 2013/0165842 A1 Jun. 27, 2013

Related U.S. Application Data

(63) Continuation of application No. 13/420,457, filed on Mar. 14, 2012, now Pat. No. 8,603,186, which is a continuation of application No. 11/300,283, filed on Dec. 15, 2005, now Pat. No. 8,147,561, which is a continuation-in-part of application No. 10/999,410, filed on Nov. 30, 2004, now Pat. No. 7,931,693.

(60) Provisional application No. 60/547,630, filed on Feb. 26, 2004.

(51) Int. Cl.
*A61F 5/00* (2006.01)
*A61M 25/04* (2006.01)
*A61F 2/04* (2013.01)
*A61M 25/10* (2013.01)

(52) U.S. Cl.
CPC .............. *A61M 25/04* (2013.01); *A61F 5/0076* (2013.01); *A61F 5/0079* (2013.01); *A61F 2002/045* (2013.01); *A61M 25/1011* (2013.01)

(58) Field of Classification Search
CPC ..... A61F 5/0003; A61F 5/003; A61F 5/0076; A61F 5/0079; A61F 2002/045
See application file for complete search history.

(56) References Cited

U.S. PATENT DOCUMENTS

| 2,773,502 A | 12/1956 | Kaslow et al. |
| 3,546,961 A | 12/1970 | Marton |
| 4,057,065 A | 11/1977 | Thow |
| 4,133,315 A | 1/1979 | Berman et al. |
| 4,134,405 A | 1/1979 | Smit |
| 4,315,509 A | 2/1982 | Smit |

(Continued)

FOREIGN PATENT DOCUMENTS

| DE | 4012642 A1 | 10/1991 |
| JP | 01015063 A2 | 1/1989 |

(Continued)

OTHER PUBLICATIONS

Burnett, Daniel R.; U.S. Appl. No. 60/490,421 entitled "Pyloric valve corking device and method," filed Jul. 28, 2003.

(Continued)

*Primary Examiner* — Thomas J Sweet
*Assistant Examiner* — Megan Wolf
(74) *Attorney, Agent, or Firm* — Shay Glenn LLP

(57) ABSTRACT

The present invention relates to methods and devices that help to curb appetite and/or reduce food intake. In one embodiment, the methods and devices of the present invention include a small intestinal/duodenal insert comprising an elongated member with at least one flow reduction element that can cause the stimulation of one or more biological signals of satiety.

18 Claims, 11 Drawing Sheets

(56) References Cited

U.S. PATENT DOCUMENTS

| | | | |
|---|---|---|---|
| 4,416,267 A | 11/1983 | Garren et al. |
| 4,485,805 A | 12/1984 | Foster, Jr. |
| 4,501,264 A | 2/1985 | Rockey |
| 4,607,618 A | 8/1986 | Angelchik |
| 4,648,383 A | 3/1987 | Angelchik |
| 4,694,827 A | 9/1987 | Weiner et al. |
| 4,878,905 A | 11/1989 | Blass |
| 4,899,747 A | 2/1990 | Garren et al. |
| 5,019,400 A | 5/1991 | Gombotz et al. |
| 5,084,061 A | 1/1992 | Gau et al. |
| 5,234,454 A | 8/1993 | Bangs |
| 5,259,399 A | 11/1993 | Brown |
| 5,329,942 A | 7/1994 | Gunther et al. |
| 5,396,880 A | 3/1995 | Kagan et al. |
| 5,439,476 A | 8/1995 | Frantzides |
| 5,484,610 A | 1/1996 | Bae |
| 5,597,797 A | 1/1997 | Clark |
| 5,820,584 A | 10/1998 | Crabb |
| 5,868,141 A | 2/1999 | Ellias |
| 6,102,922 A | 8/2000 | Jakobsson et al. |
| 6,160,084 A | 12/2000 | Langer et al. |
| 6,187,330 B1 | 2/2001 | Wang et al. |
| 6,264,700 B1 | 7/2001 | Kilcoyne et al. |
| 6,267,988 B1 | 7/2001 | Meyer |
| 6,302,917 B1 | 10/2001 | Dua et al. |
| 6,306,163 B1 | 10/2001 | Fitz |
| 6,336,934 B1 | 1/2002 | Gilson et al. |
| 6,365,173 B1 | 4/2002 | Domb et al. |
| 6,388,043 B1 | 5/2002 | Langer et al. |
| 6,402,687 B1 | 6/2002 | Ouchi |
| 6,540,789 B1 | 4/2003 | Silverman et al. |
| 6,579,301 B1 | 6/2003 | Bales et al. |
| 6,635,431 B1 | 10/2003 | Bihain et al. |
| 6,685,957 B1 | 2/2004 | Bezemer et al. |
| 6,716,444 B1 | 4/2004 | Castro et al. |
| 6,720,402 B2 | 4/2004 | Langer et al. |
| 6,740,121 B2 | 5/2004 | Geitz |
| 6,800,056 B2 | 10/2004 | Tartaglia et al. |
| 6,939,557 B2 | 9/2005 | Rowe et al. |
| 6,946,002 B2 | 9/2005 | Geitz |
| 6,953,560 B1 | 10/2005 | Castro et al. |
| 7,025,791 B2 | 4/2006 | Levine et al. |
| 7,037,344 B2 | 5/2006 | Kagan et al. |
| 7,111,627 B2 | 9/2006 | Stack et al. |
| 7,121,283 B2 | 10/2006 | Stack et al. |
| 7,122,058 B2 | 10/2006 | Levine et al. |
| 7,175,669 B2 | 2/2007 | Geitz |
| 7,223,277 B2 | 5/2007 | DeLegge |
| 7,335,210 B2 | 2/2008 | Smit |
| 7,476,256 B2 * | 1/2009 | Meade et al. | 623/23.64 |
| 7,931,693 B2 | 4/2011 | Binmoeller |
| 8,147,561 B2 | 4/2012 | Binmoeller |
| 2002/0002384 A1 | 1/2002 | Gilson et al. |
| 2002/0035347 A1 | 3/2002 | Bagaoisan et al. |
| 2002/0035361 A1 | 3/2002 | Houser et al. |
| 2002/0111648 A1 | 8/2002 | Kusleika et al. |
| 2002/0183853 A1 | 12/2002 | Mitchell et al. |
| 2003/0040804 A1 | 2/2003 | Stack et al. |
| 2003/0199990 A1 | 10/2003 | Stack et al. |
| 2004/0015187 A1 | 1/2004 | Lendlein et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0088022 A1 | 5/2004 | Chen |
| 2004/0092892 A1 | 5/2004 | Kagan et al. |
| 2004/0110285 A1 | 6/2004 | Lendlein et al. |
| 2004/0122456 A1 | 6/2004 | Saadat et al. |
| 2004/0153118 A1 | 8/2004 | Clubb et al. |
| 2004/0219186 A1 | 11/2004 | Ayres |
| 2004/0267378 A1 | 12/2004 | Gazi et al. |
| 2005/0004681 A1 | 1/2005 | Stack et al. |
| 2005/0033331 A1 | 2/2005 | Burnett et al. |
| 2005/0038415 A1 | 2/2005 | Rohr et al. |
| 2005/0049718 A1 | 3/2005 | Dann et al. |
| 2005/0055014 A1 | 3/2005 | Coppeta et al. |
| 2005/0055039 A1 | 3/2005 | Burnett et al. |
| 2005/0075405 A1 | 4/2005 | Wilson et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0090873 A1 | 4/2005 | Imran |
| 2005/0119674 A1 | 6/2005 | Gingras |
| 2005/0125020 A1 | 6/2005 | Meade et al. |
| 2005/0125075 A1 | 6/2005 | Meade et al. |
| 2005/0183732 A1 | 8/2005 | Edwards |
| 2005/0238694 A1 | 10/2005 | Gerhardt et al. |
| 2005/0245719 A1 | 11/2005 | Mather et al. |
| 2005/0267595 A1 | 12/2005 | Chen et al. |
| 2005/0273060 A1 | 12/2005 | Levy et al. |
| 2005/0277975 A1 | 12/2005 | Saadat et al. |
| 2006/0020278 A1 | 1/2006 | Burnett et al. |
| 2006/0033332 A1 | 2/2006 | Wilson |
| 2006/0064120 A1 | 3/2006 | Levine et al. |
| 2006/0079944 A1 | 4/2006 | Imran |
| 2006/0086362 A1 | 4/2006 | Solomon |
| 2006/0129237 A1 | 6/2006 | Imran |
| 2006/0142794 A1 | 6/2006 | Lendlein et al. |
| 2006/0155311 A1 | 7/2006 | Hashiba et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0247718 A1 | 11/2006 | Starkebaum |
| 2006/0259051 A1 | 11/2006 | Nissl |
| 2006/0265082 A1 | 11/2006 | Meade et al. |
| 2006/0282107 A1 | 12/2006 | Hashiba et al. |
| 2007/0005147 A1 | 1/2007 | Levine et al. |
| 2007/0010864 A1 | 1/2007 | Dann et al. |
| 2007/0010865 A1 | 1/2007 | Dann et al. |
| 2007/0027548 A1 | 2/2007 | Levine et al. |
| 2007/0083271 A1 | 4/2007 | Levine et al. |
| 2007/0110793 A1 | 5/2007 | Kantrowitz et al. |
| 2007/0135768 A1 | 6/2007 | Carlsen |
| 2007/0156159 A1 | 7/2007 | Gannoe et al. |
| 2007/0156248 A1 | 7/2007 | Marco et al. |
| 2007/0265598 A1 | 11/2007 | Karasik |
| 2007/0282418 A1 | 12/2007 | Weitzner |
| 2007/0293885 A1 | 12/2007 | Binmoeller et al. |
| 2008/0065136 A1 | 3/2008 | Young |
| 2008/0234834 A1 | 9/2008 | Meade et al. |
| 2009/0187206 A1 | 7/2009 | Binmoeller et al. |
| 2011/0137227 A1 | 6/2011 | McKinley et al. |
| 2011/0190684 A1 | 8/2011 | Binmoeller |
| 2012/0172999 A1 | 7/2012 | Binmoeller |
| 2013/0109912 A1 | 5/2013 | Binmoeller et al. |
| 2015/0305906 A1 | 10/2015 | Mckinley et al. |

FOREIGN PATENT DOCUMENTS

| | | |
|---|---|---|
| JP | 2004509714 | 4/2004 |
| WO | WO 89/00407 A1 | 1/1989 |
| WO | WO 96/01591 A1 | 1/1996 |
| WO | WO 03/094785 A1 | 11/2003 |
| WO | WO 2004/041133 A1 | 5/2004 |
| WO | WO 2004/093753 A2 | 11/2004 |
| WO | WO 2005/120363 A1 | 12/2005 |
| WO | WO 2006/044640 A1 | 4/2006 |
| WO | WO 2006/092789 A2 | 9/2006 |
| WO | WO 2006/102240 A2 | 9/2006 |
| WO | WO 2007/030829 A2 | 3/2007 |
| WO | WO 2007/053556 A1 | 5/2007 |
| WO | WO 2007/053706 A1 | 5/2007 |
| WO | WO 2007/053707 A1 | 5/2007 |
| WO | WO 2007/075396 A2 | 7/2007 |
| WO | WO 2008/001381 A2 | 1/2008 |

OTHER PUBLICATIONS

Burnett, Daniel R.; U.S. Appl. No. 60/525,105 entitled "Intragastric therapeutic device and method," filed Nov. 28, 2003.

Asakawa et al., "Characterization of the effects of pancreatic polypeptide in the regulation of energy balance," Gastroenterology 124(5):1325-36 (May 2003).

(56) References Cited

OTHER PUBLICATIONS

Batterham et al., "Gut hormone PYY(3-36) physiologically inhibits food intake," Nature 418(6898): 650-4 (Aug. 8, 2002).
Batterham et al., "Inhibition of food intake in obese subjects by peptide YY3-36,"N Engl J Med., 349(10):941-8 (Sep. 4, 2003).
Batterham et al., "Pancreatic polypeptide reduces appetite and food intake in humans," J Clin Endocrinol Metab. 88(8):3989-92 (Aug. 2003).
Caro et al., "Leptin: the tale of obesity gene," Diabetes 45(11): 1455-62 (Nov. 1996).
Chapman et al., "Effects of small-intestinal fat and carbohydrate infusions on appetite and food intake in obese and nonobese men," Am J Clin Nutr, vol. 69, pp. 6-12 (Jan. 1999).
Cohen et al., "Oxyntomodulin suppresses appetite and reduces food intake in humansm" J Clin Endocrinol Metab., 88(10): 4696-4701 (Oct. 2003).
Collins et al., "Role of leptin in fat regulation," Nature, 380 (6576):677 (Apr. 25, 1996).
D'Alessio et al., "Activation of the parasympathetic nervous system is necessary for normal meal-induced insulin secretion in rhesus macaques," J Clin Endocrinol Metab., 86(3): 1253-9 (Mar. 2001).
Davis et al., "Distension of the small intestine, satiety, and the control of food intake," Am Journal of Clinical Nutrition, vol. 31, pp. S255-S258 (Oct. 1978).
de Castro et al., "A general model of intake regulation," Neuroscience and Behavioral Reviews, vol. 26(5), pp. 581-595 (Aug. 2002).
French et al., "Is Cholecystokinin a Satiety Hormone? Correlations of Plasma Cholecystokinin with Hunger, Satiety, and Gastric Emptying in Normal Volunteers," Appetite. vol. 16, pp. 95-104 (Oct. 1993).
Gao et al., "Sensory and biomechanical responses to ramp-controlled distension of the human duodenum," Am. J. Physiol. Gas., vol. 284, pp. G461-G471 (Mar. 2003).
Geliebter et al., "Clinical trial of silicone rubber gastric balloon to treat obesity," Int J Obesity, 15(4): 259-266 (Apr. 1991).
Ghatei et al., "Molecular forms of human enteroglucagon in tissue and plasma; plasma responses to nutrient stimuli in health and in disorders of the upper gastrointestinel tract." J Clin Endocrinol Metab, 57(3): 488-95 (Sep. 1983).
Gibbs et al., "Cholecystokinin descreases food intake in rats," J Comp Physiol Psychol. 84(3):488-95 (Sep. 1973).
Havel, Peter, "Peripheral signals conveying metabolic information to the brain: Short-term and long-term regulation of food intake and energy homeostasis," Society for Experiment Biology and Medicine, vol. 226, pp. 963-977 (Dec. 2001).
Havel, PJ, "Role of adipose tissue in body-weight regulation: mechanisms regulating leptin production and energy balance," Proc Nutr Soc. 59(3):359-71 (Aug. 2000).
Haynes et al., "Receptor-mediated regional sympathetic nerve activation by leptin," J Clin Invest. 100(2): 270-278 (Jul. 15, 1997).
Herrmann et al., "Glucagon-like peptide-1 and glucose-dependent insulin-releasing polypeptide plasma levels in response to nutrients," Digestion 56(2):117-26; (year of publication is sufficiently earlier than the effective U.S. filing date and any foreign priority date ) 1995.
Kissileff et al., "Cholecystokinin and stomach distension combine to reduce food intake in humans," Am J Physiol Regul Integr Comp Physiol., 285(5):R992-8 (Nov. 2003).
Le Quellec et al., "Oxyntomodulin-like immunoreactivity: diurnal profile of a new potential entergastrone," J Clin Endorcrinol Metab, 74(6): 1405-9 (Jun. 1992).
Levin et al., "Decreased food intake does not completely account for adiposity reduction after ob protein infusion," Proc. Natl Acad Sci U.S.A., 93(4): 1726-30 (Feb. 20, 1996).
Liddle et al., "Cholecystokinin bioactivity in human plasma. Molecular forms, responses to feeding, and relationship to gallbladder contraction," J Clin Invest. 75(4):1144-52 (Apr. 1985).
Lindor et al., "Intragastric ballons in comparison with standard therapy for obesity—a randomized, double-blind trial," Mayo Clin Proc 62(11): 992-6 (Nov. 1987).
Malaisse-Lagae et al., "Pancreatic polypeptide: a possible role in the regulation of food intake in the mouse. (Hypothesis)" Experientia 15; 33(7):915-917 (Jul. 15, 1977).
Mathus-Vliegen et al., "Intragastric ballon in the treatment of super-morbid obesity, Double-blind sham-controlled, crossover eevealuation of 500-millimeter ballon," Gastroenterology, 99(2): 362-369 (Aug. 1990).
Moran el al, "Neurobiology of cholecystokinin," Crit Rev Neurobiol. 9(1): 1-28 (year of publication is sufficiently earlier than the effective U.S. filing date and any foreign priority date) 1994.
Moran et al., "Gastrointestinal satiety signals," Am J Physiol Gastrointest Liver Physiol, vol. 286, pp. G183-G188 (Feb. 1, 2004).
Näslund et al., "GLP-1 slows solid gastric emptying and inhibits insulin, glucagon, and PYY release in humans, " Am J Physiol 277 (3 Pt 2):R910-R916 (Sep. 1999).
Rayner et al., "Effects of cholecystokinin on appetite and pyloric motility during physiological hyperglycermia," Am j. Physiol. Gastrointest. Liver Physiol., vol. 278, pp. G98-G104 (Jan. 2000).
Read et al., "The Role of the Gut in Regulating Food Intake in Man," Nutrition Reviews, vol. 52, pp. 1-10 (Jan. 1994).
Read, N.W. "Role of gastrointestinal factors in hunger and satiety in man, " Proceedings of the Nutrition Society, vol. 51, pp. 7-11 (May 1992).
Remington: The Science and Practice of Pharmacy, 20th Ed., Chap. 47, Controlled Release Drug Delivery Systems. (Jun. 2003).
Remington's Pharmaceutical Sciences, 17th Ed.; A. R. Gennaro (Editor); "Freeze-drying," p. 1538-1539 (year of publication is sufficiently earlier than the effective U.S. filing date and any foreign priority date) 1985.
Rigaud et al., "Gastric distension, hunger, and energy intake after ballon implantation in severe obesity," Int J Obes Relat Metab Disor., 19(7):489-95 (Jul. 1995).
Ritter, Robert C.; Gastrointestinal mechanisms of satiation for food; Physiol Behav.; 81(2):249-73; Apr. 2004.
Scarpace et al., "Leptin increases uncoupling protein expression and energy expenditure," Am J Physiol., 273 (1 Pt 1): E226-230 (Jul. 1997).
Schirra et al., Mechanisms of the antidiabetic action of subcutaneous glucagon-like peptide-1 (7-36)amide in non-insulin dependent diabetes mellitus, J Endocrinol. 156(1):177-86 (Jan. 1998).
Schwartz et al., "Central nervous system control of food intake," Nature, 404(6778): 661-671 (Apr. 6, 2000).
Schwartz et al., "Keeping hunger at bay," Nature, vol. 418, pp. 595-597; Aug 8, 2002.
Schwartz et al., "Model for the regulation of energy balance and adiposity by the central nervous system," Am J Clin Nutr., 69(4): 584-96 (Apr. 1999).
Standring, Susan (ed). Gray's Anatomy, 39th Ed. 1163-64; Nov. 24, 2004.
Wilding, J. P. H., "Neuropeptides and appetite control," Diabetes U.K. Diabetic Medicine, vol. 19, pp. 619-627 (Aug. 2002).
Woods et al., "The Regulation of Food Intake by Peptides," Annals of the New York Academy of Sciences, vol. 575. pp. 236-243; Dec. 1989.
Wynne et al., "Appetite control," Journal of Endocrinology, vol. 184, pp. 291-318; Feb. 2005.
McKinley et al.; U.S. Appl. No. 13/769,097 entitled "Methods and devices for delivering or delaying lipids within a duodenum," filed Feb. 15, 2013.
Binmoeller et al.; U.S. App. No. 14/062,744 entitled "Methods and Devices to Curb Appetite and/or to Reduce Food Intake," filed Oct. 24, 2013.
Binmoeller; U.S. Appl. No. 14/101,241 entitled "Method and Apparatus for Reducing Obesity," filed Dec. 9, 2013.
Binmoeller et al.; U.S. Appl. No. 14/748,065 entitled "Conformationally-stabilized intraluminal device for medical applications," filed Jun. 23, 2015.

\* cited by examiner

METHODS AND DEVICES TO CURB APPETITE AND/OR REDUCE FOOD INTAKE

CROSS REFERENCE TO RELATED APPLICATIONS

This application is a continuation of U.S. patent application Ser. No. 13/420,457, filed Mar. 14, 2012, and titled "METHODS AND DEVICES TO CURB APPETITE AND/ OR REDUCE FOOD INTAKE," now Publication No. US-2012-0172999-A1, which is a continuation of U.S. patent application Ser. No. 11/300,283, filed Dec. 15, 2005, and titled "METHODS AND DEVICES TO CURB APPETITE AND/OR REDUCE FOOD INTAKE," now U.S. Pat. No. 8,147,561, which is a continuation-in-part of U.S. patent application Ser. No. 10/999,410, filed Nov. 30, 2004, and titled "METHOD AND APPARATUS FOR REDUCING OBESITY," now U.S. Pat. No. 7,931,693, which claims priority to U.S. Provisional Patent Application No. 60/547,630, filed Feb. 26, 2004 and titled "METHOD AND APPARATUS FOR REDUCING OBESITY." Each of these patent applications are herein expressly incorporated by reference in their entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to methods and devices that help to curb appetite and/or to reduce food intake (hereinafter "reduce food intake").

BACKGROUND

Obesity, defined as a body mass index (BMI) of greater than 30, is a major health concern in the United States and other countries. Current research suggests that one in three Americans and more than 300 million people world-wide are obese. www.who.int/nut/obs.htm (last visited Dec. 13, 2005). Complications of obesity include many serious and life-threatening diseases including hypertension, diabetes, coronary artery disease, stroke, congestive heart failure, pulmonary insufficiency, multiple orthopedic problems, various cancers and a markedly decreased life expectancy. Intentional weight loss, however, can improve many of these medical complications associated with obesity.

While weight loss can improve many of the medical complications associated with obesity, its management as a health concern has proven troublesome. A variety of approaches including dietary methods, psychotherapy, behavior modification, and pharmacotherapy have failed to control the rapid growth in the incidence and severity of obesity seen in the United States. According to the Center for Disease Control, obesity contributes to about 111,909 deaths annually, just behind tobacco (435,000) and ahead of alcohol (85,000), car accidents (43,000) and guns (29,000). Mokdad et al., 291 (10), JAMA 1238-1245 (2004); Flegal et al., 293(15) JAMA 1861-1867 (2005). Further, the estimated annual cost of obesity in the U.S. in 2000 was about $117 billion. Centers for Disease Control and Prevention available at http://www.cdc.gov/nccdphp/aag/aag_dnpa.html (last visited Nov. 11, 2005).

The severity of problems associated with obesity has led to the development of several drastic surgical procedures. One such procedure physically reduces the size of the stomach so that a person cannot consume as much food as was previously possible. These stomach reduction surgeries had limited early success, but now it is known that the stomach can restretch over time, limiting the achievement of sustained weight loss in many individuals. Another drastic surgical procedure induces the malabsorption of food by reducing the absorptive surface of the gastrointestinal (GI) tract, generally via bypassing portions of the small intestine. This gastric by-pass procedure further has been combined with stomach reduction surgery. While these described surgical procedures can be effective to induce a reduction in food intake and/or overall weight loss in some, the surgical procedures are highly invasive and cause undue pain and discomfort. Further, the described procedures may result in numerous life-threatening postoperative complications. These surgical procedures are also expensive, difficult to reverse, and place a large burden on the national health care system.

Non-surgical approaches for the treatment of obesity also have been developed. For example, one non-surgical endoscopic approach to treating obesity includes the placement of a gastric balloon within the stomach. The gastric balloon fills a portion of the stomach, providing the patient with a feeling of fullness, thereby reducing food intake. Many problems are associated with the gastric balloon device, however, including poor patient tolerance and complications due to rupture and/or migration of the balloon. Further, sham-controlled studies have failed to show that implantation of a gastric balloon produces a better reduction in food intake than dieting alone. Trostler et al., 19(7) Int. J. Obes. Relat. Metab. Disord. 489-495 (1995); Geliebter et al. 15(4) Int J Obes. 259-266 (1991); Mathus-Vliegen et al., 99(2) Gastroenterol. 362-369 (1990); Lindor et al., 62(11) Mayo Clin. Proc. 992-996 (1987).

Other non-surgical devices designed to induce weight loss limit the absorption of nutrients in the small intestine by funneling food from the stomach into a tube found within the small intestine so that the food is not fully digested or absorbed within the small intestine. While this type of device may be somewhat effective at limiting the absorption of consumed food, there is still room for a variety of improvements in non-surgical devices designed to induce weight loss and/or a reduction in food intake.

An understanding of biological events that contribute to the creation of satiety signals provides an opportunity to develop "smart" nonsurgical devices that can trigger such events. The amount of food that individuals consume is largely dependent on biological signals between the gut and the brain. Specifically, hormonal signals from the gut to the brain are correlated with both the onset and cessation of food intake. While increased levels of hormones such as ghrelin, motilin and agouti-related peptide are involved in the promotion of appetite and the onset of food intake, increased levels of a number of other hormones are involved in the cessation of food intake.

Various biologic events contribute to the physiologic cessation of food intake. Generally, as a meal is consumed, the ingested food and by-products of digestion interact with an array of receptors along the GI tract to create satiety signals. Satiety signals communicate to the brain that an adequate amount of food has been consumed and that an organism should stop eating. Specifically, GI tract chemoreceptors respond to, without limitation, products of digestion (such as sugars, fatty acids, amino acids and peptides) while stretch and mechanoreceptors in the stomach and proximal small intestine respond to, without limitation, the physical presence of consumed foods. Chemoreceptors respond to the products of digestion by, without limitation, causing the release of hormones or other molecular signals. These released hormones and/or other molecular signals can stimulate nerve fibers to send satiety signals to the brain. The arrival of these signals in the brain can trigger a variety of neural pathways that can reduce food intake. The released hormones and/or other molecular signals can also travel to the brain themselves to help create signals of satiety. Stretch and mechanoreceptors generally send satiety signals to the brain through, without limitation, stimulation of nerve fibers in the periphery that signal the brain. The present invention provides methods and devices that help to reduce food intake by providing non-surgical devices that trigger the aforementioned biological events that contribute to the creation of satiety signals.

SUMMARY OF THE DISCLOSURE

The present invention provides methods and devices to reduce food intake by one or more of: (i) slowing the passage of food so that food remains in the GI tract for a longer period of time and thereby triggers satiety signals for a longer period of time; (ii) stimulating stretch and mechanoreceptors within the GI tract to send satiety signals to the brain to decrease the likelihood or amount of food intake; and/or (iii) stimulating chemoreceptors within the GI tract to send satiety signals to the brain to decrease the likelihood or amount of food intake.

In one embodiment the present invention includes a duodenal/small intestinal insert comprising an elongated member wherein the elongated member has a proximal end and a distal end; an anchoring member engaged with the proximal end of the elongated member; and at least one flow reduction element on the elongated member wherein when the anchoring member is anchored the at least one flow reduction element is in the small intestine of the organism and wherein when the duodenal/small intestinal insert is placed within an organism in this manner, the insert triggers an initial physiological effect that contributes to the creation of one or more biological signals of satiety.

Another device of the present invention includes a duodenal/small intestinal insert comprising an elongated member with at least one angle and at least one flow reduction element wherein the at least one angle matches an angle in the small intestine of an organism and wherein the at least one flow reduction element has a diameter that matches the diameter of the small intestine of the organism and wherein the at least one angle and the at least one flow reduction element allow the duodenal/small intestinal insert to lodge in the small intestine of the organism such that it remains in the small intestine for a period of time. In one embodiment of this device of the present invention, the insert triggers an initial physiological effect that contributes to the creation of one or more biological signals of satiety.

In another embodiment of the devices of the present invention, the triggering of the initial physiological effect is caused by the slowing of the passage of consumed food through the GI tract of the organism. In another embodiment of the devices of the present invention, the diameter of the at least one flow reduction element is sized to restrict but not occlude the movement of consumed foods through the small intestine. In another embodiment of the devices of the present invention, the diameter of the at least one flow reduction element is about 1 cm. In another embodiment of the devices of the present invention, the diameter of the at least one flow reduction element is about 2 cm. In another embodiment of the devices of the present invention, the diameter of the at least one flow reduction element is about 3 cm.

In another embodiment of the devices of the present invention, the duodenal/small intestinal insert triggers an initial physiological effect by releasing bioactive material(s) from the duodenal/small intestinal insert. In one embodiment of the devices of the present invention, the bioactive material is a by-product of digestion selected from the group consisting of sugars, fatty acids, amino acids and peptides. In another embodiment of the devices of the present invention the bioactive material is a drug. In another embodiment of the devices of the present invention the bioactive material is a drug selected from one or more of the group consisting of altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin, penicillin, ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, cefaclor, cephalothin, cefadroxil, cephapirin, cefamandole, cephradine, cefatrizine, cefsulodin, cefazolin, ceftazidim, ceforanide, ceftriaxon, cefoxitin, cefuroxime, cephacetrile, latamoxef, cephalexin, amikacin, neomycin, dibekacyn, kanamycin, gentamycin, netilmycin, kanamycin, tobramycin, amphotericin B, novobiocin, bacitracin, nystatin, clindamycin, polymyxins, colistin, rovamycin, erythromycin, spectinomycin, lincomycin, vancomycin, chlortetracycline, oxytetracycline, demeclocycline, rolitetracycline, doxycycline, tetracycline, minocycline, chloramphenicol, rifamycin, rifampicin, thiamphenicol, sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole, trimethoprim with sulfamethoxazole, sulfametrole, methanamine, norfloxacin, cinoxacin, nalidixic acid, nitrofurantoin, nifurtoinol, oxolinic acid; metronidazole; aminosalicyclic acid, isoniazide, cycloserine, rifampicine, ethambutol, tiocarlide, ethionamide, viomycin; amithiozone, rifampicine, clofazimine, sodium sulfoxone, diaminodiphenylsulfone, amphotericin B, ketoconazole, clotrimazole, miconazole, econazole, natamycin, flucytosine, nystatine, griseofulvin, aciclovir, idoxuridine, amantidine, methisazone, cytarabine, vidarabine, ganciclovir, chloroquine, iodoquinol, clioquinol, metronidazole, dehydroemetine, paromomycin, diloxanide, furoatetinidazole, emetine, chloroquine, pyrimethamine, hydroxychloroquine, quinine, mefloquine, sulfadoxine/pyrimethamine, pentamidine, sodium suramin, primaquine, trimethoprim, proguanil, antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole, niclosamide, acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen, tolmetin, colchicine, allopurinol, alfentanil, methadone, bezitramide, morphine, buprenorfine, nicomorphine, butorfanol, pentazocine, codeine, pethidine, dextromoramide, piritranide, dextropropoxyphene, sufentanil, fentanyl, articaine, mepivacaine, bupivacaine, prilocalne, etidocaine, procaine, lidocaine, tetracaine, amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide, trihexyphenidyl, baclofen, carisoprodol, chlormezanone, chlorzoxazone, cyclobenzaprine, dantrolene, diazepam, febarbamate, mefenoxalone, mephenesin, metoxalone, methocarbamol, tolperisone, levothyronine, liothyronine, carbimazole, methimazole, methylthiouracil and propylthiouracil.

In another embodiment of the devices of the present invention the bioactive material is a hormone. In another embodiment of the devices of the present invention the bioactive material is a natural or synthetic hormone selected from one or more of the group consisting of cortisol, deoxycorticosterone, fluorohydrocortisone, beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone, triamcinolone (acetonide), danazole, fluoxymesterone, mesterolone, dihydrotestosterone methyltestosterone, testosterone, dehydroepiandrosetone, dehydroepiandrostendione, calusterone, nandrolone, dromostanolone, oxandrolone, ethylestrenol, oxymetholone, methandriol, stanozolol methandrostenolone, testolactone, cyproterone acetate, diethylstilbestrol, estradiol, estriol, ethinylestradiol, mestranol, quinestrol chlorotrianisene, clomiphene, ethamoxytriphetol, nafoxidine, tamoxifen, allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, progesterone, inhibin, antidiuretic hormone, proopiomelanocortin, follicle stimulating hormone, prolactin, angiogenin, epidermal growth factor, calcitonin, erythropoietin, thyrotropic releasing hormone, insulin, growth hormones, human chorionic gonadotropin, luteinizing hormone, adrenocorticotropic hormone (ACTH), lutenizing hormone releasing hormone (LHRH), parathyroid hormone (PTH), thyrotropin releasing hormone (TRH), vasopressin, and corticotropin releasing hormone.

In another embodiment of the devices of the present invention the triggering of the initial physiological effect that contributes to the creation of one or more biological satiety signals is caused by contract and/or pressure exerted on the wall of the small intestine by the duodenal/small intestinal insert.

In another embodiment of the devices of the present invention the initial triggering occurs through activation of at least one chemoreceptor. In another embodiment of the devices of the present invention the initial triggering occurs through the activation of at least one stretch receptor. In another embodiment of the devices of the present invention the initial triggering occurs through the activation of at least one mechanoreceptor.

In another embodiment of the devices of the present invention the one or more biological signals of satiety is transmitted at least in part through stimulation of afferent nerve fibers. In another embodiment of the devices of the present invention the afferent nerve fibers are vagal afferent nerve fibers.

In another embodiment of the devices of the present invention the one or more biological signals of satiety is transmitted at least in part by molecules released as a result of stimulation of the chemoreceptor. In another embodiment of the devices of the present invention the molecules are hormones. In another embodiment of the devices of the present invention the molecules are selected from one or more of the group consisting of cholecystokinin, peptide $YY_{3-36}$, glucagon-like peptide 1, gastric-inhibitory peptide, neurotensin, amylin, leptin, bombesin, calcitonin, calcitonin gene-related peptide, somatostatin, neuromedin U and glucagon.

In another embodiment of the devices of the present invention the molecules activate a receptor in the periphery to cause a subsequent physiological effect. In another embodiment of the devices of the present invention the molecules activate a receptor in the liver to cause a subsequent physiological effect. In another embodiment of the devices of the present invention the molecules activate a receptor in the pylorus to cause a subsequent physiological effect. In another embodiment of the devices of the present invention the molecules activate a receptor in the stomach to cause a subsequent physiological effect. In another embodiment of the devices of the present invention the molecules travel to the brain to activate a receptor to cause a subsequent physiological effect.

In another embodiment of the devices of the present invention, the elongated member further comprises at least one angle that matches an angle of said organism's small intestine. In another embodiment of the devices of the present invention the elongated member further comprises an angle of about 70°. In another embodiment of the devices of the present invention the elongated member further comprises an angle of about 71°. In another embodiment of the devices of the present invention the elongated member further comprises an angle of about 72°. In another embodiment of the devices of the present invention the elongated member further comprises an angle of about 73°. In another embodiment of the devices of the present invention the elongated member further comprises an angle of about 74°. In another embodiment of the devices of the present invention the elongated member further comprises an angle of about 75°. In another embodiment of the devices of the present invention the elongated member further comprises an angle of about 76°. In another embodiment of the devices of the present invention the elongated member further comprises an angle of about 77°. In another embodiment of the devices of the present invention the elongated member further comprises an angle of about 78°. In another embodiment of the devices of the present invention the elongated member further comprises an angle of about 79°. In another embodiment of the devices of the present invention the elongated member further comprises an angle of about 80°. In another embodiment of the devices of the present invention the elongated member further comprises an angle of about 81°. In another embodiment of the devices of the present invention the elongated member further comprises an angle of about 82°. In another embodiment of the devices of the present invention the elongated member further comprises an angle of about 83°. In another embodiment of the devices of the present invention the elongated member further comprises an angle of about 84°. In another embodiment of the devices of the present invention the elongated member further comprises an angle of about 85°. In another embodiment of the devices of the present invention the elongated member further comprises an angle of about 86°. In another embodiment of the devices of the present invention the elongated member further comprises an angle of about 87°. In another embodiment of the devices of the present invention the elongated member further comprises an angle of about 88°. In another embodiment of the devices of the present invention the elongated member further comprises an angle of about 89°. In another embodiment of the devices of the present invention the elongated member further comprises an angle of about 90°. In another embodiment of the devices of the present invention, the elongated member comprises two angles, each matching an angle of said organism's small intestine.

The present invention also includes methods. In one embodiment the methods of the present invention include placing a duodenal/small intestinal insert in the small intestine of an organism wherein the duodenal/small intestinal insert comprises an elongated member with at least one angle and at least one flow reduction element wherein the at least one angle matches an angle in the small intestine of an organism and wherein the at least one flow reduction element has a diameter that is less than the diameter of the small intestine of the organism and wherein the at least one angle and the at least one flow reduction element allow the duodenal/small intestinal insert to lodge in the small intestine of the organism such that it remains in the small intestine for a period of time. In one embodiment of this method of the present invention the duodenal/small intestinal insert triggers an initial physiological effect that contributes to the creation of one or more biological signals of satiety. In another embodiment of the methods of the present invention, the diameter is sized to restrict but not occlude the movement of digested food through the small intestine. In another embodiment of the methods of the present invention, the diameter is about 1 cm. In another embodiment of the methods of the present invention, the diameter is about 2 cm. In another embodiment of the methods of the present invention, the diameter is about 3 cm.

Another embodiment of the methods of the present invention include a method for reducing food intake wherein the method comprises positioning a duodenal/small intestinal insert in an organism wherein the insert comprises an elongated member with a proximal end and a distal end; an anchoring member engaged with the proximal end of the elongated member; and at least one flow reduction element on the elongated member wherein when the anchoring member is anchored the at least one flow reduction element is in the small intestine of the organism, and when the insert is so placed, the duodenal/small intestinal insert triggers an initial physiological effect that contributes to the creation of one or more biological signals of satiety.

In another embodiment of the methods of the present invention, the triggering of the initial physiological effect is caused by the slowing of the passage of consumed food through the small intestine of the organism.

In another embodiment of the methods of the present invention, the triggering of the initial physiological effect is caused by the release of a bioactive material from the duodenal/small intestinal insert. In another embodiment of the methods of the present invention, the bioactive material is a by-product of digestion selected from the group consisting of sugars, fatty acids, amino acids and peptides. In another embodiment of the methods of the present invention, the bioactive material is a drug. In another embodiment of the methods of the present invention the bioactive material is a drug selected from one or more of the group consisting of altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin, penicillin, ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, cephalexin, amikacin, neomycin, dibekacyn, kanamycin, gentamycin, netilmycin, kanamycin, tobramycin, amphotericin B, novobiocin, bacitracin, nystatin, clindamycin, polymyxins, colistin, rovamycin, erythromycin, spectinomycin, lincomycin, vancomycin, chlortetracycline, oxytetracycline, demeclocycline, rolitetracycline, doxycycline, tetracycline, minocycline, chloramphenicol, rifamycin, rifampicin, thiamphenicol, sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole, trimethoprim with sulfamethoxazole, sulfametrole, methanamine, norfloxacin, cinoxacin, nalidixic acid, nitrofurantoine, nifurtoinol, oxolinic acid; metronidazole; aminosalicyclic acid, isoniazide, cycloserine, rifampicine, ethambutol, tiocarlide, ethionamide, viomycin; amithiozone, rifampicine, clofazimine, sodium sulfoxone, diaminodiphenylsulfone, amphotericin B, ketoconazole, clotrimazole, miconazole, econazole, natamycin, flucytosine, nystatine, griseofulvin, aciclovir, idoxuridine, amantidine, methisazone, cytarabine, vidarabine, ganciclovir, chloroquine, iodoquinol, clioquinol, metronidazole, dehydroemetine, paromomycin, diloxanide, furoatetinidazole, emetine, chloroquine, pyrimethamine, hydroxychloroquine, quinine, mefloquine, sulfadoxine/pyrimethamine, pentamidine, sodium suramin, primaquine, trimethoprim, proguanil, antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole, niclosamide, acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen, tolmetin, colchicine, allopurinol, alfentanil, methadone, bezitramide, morphine, buprenorfine, nicomorphine, butorfanol, pentazocine, codeine, pethidine, dextromoramide, piritranide, dextropropoxyphene, sufentanil, fentanyl, articaine, mepivacaine, bupivacaine, prilocalne, etidocaine, procaine, lidocaine, tetracaine, amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide, trihexyphenidyl, baclofen, carisoprodol, chlormezanone, chlorzoxazone, cyclobenzaprine, dantrolene, diazepam, febarbamate, mefenoxalone, mephenesin, metoxalone, methocarbamol, tolperisone, levothyronine, liothyronine, carbimazole, methimazole, methylthiouracil and propylthiouracil.

In another embodiment of the methods of the present invention, the bioactive material is a hormone. In another embodiment of the methods of the present invention the bioactive material is a natural or synthetic hormone selected from one or more of the group consisting of cortisol, deoxycorticosterone, fluorohydrocortisone, beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone, triamcinolone (acetonide), danazole, fluoxymesterone, mesterolone, dihydrotestosterone methyltestosterone, testosterone, dehydroepiandrosetone, dehydroepiandrostendione, calusterone, nandrolone, dromostanolone, oxandrolone, ethylestrenol, oxymetholone, methandriol, stanozolol methandrostenolone, testolactone, cyproterone acetate, diethylstilbestrol, estradiol, estriol, ethinylestradiol, mestranol, quinestrol chlorotrianisene, clomiphene, ethamoxytriphetol, nafoxidine, tamoxifen, allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, progesterone, inhibin, antidiuretic hormone, proopiomelanocortin, follicle stimulating hormone, prolactin, angiogenin, epidermal growth factor, calcitonin, erythropoietin, thyrotropic releasing hormone, insulin, growth hormones, human chorionic gonadotropin, luteinizing hormone, adrenocorticotropic hormone (ACTH), lutenizing hormone releasing hormone (LHRH), parathyroid hormone (PTH), thyrotropin releasing hormone (TRH), vasopressin, and corticotropin releasing hormone.

In another embodiment of the methods of the present invention, the triggering of the initial physiological effect that contributes to the creation of one or more biological signals of satiety is caused by contact and/or pressure exerted on the wall of the small intestine of the organism by the duodenal/small intestinal insert.

In another embodiment of the methods of the present invention, the triggering of the initial physiological effect occurs through the activation of at least one chemoreceptor. In another embodiment of the methods of the present invention, the triggering of the initial physiological effect occurs through the activation of at least one stretch receptor. In another embodiment of the methods of the present invention, the triggering of the initial physiological effect occurs through the activation of at least one mechanoreceptor.

In another embodiment of the methods of the present invention, the one or more biological signals of satiety is transmitted at least in part through stimulation of afferent nerve fibers. In another embodiment of the methods of the present invention, the afferent nerve fibers are vagal afferent nerve fibers.

In another embodiment of the methods of the present invention, the one or more biological signals of satiety is transmitted at least in part by molecules released as a result of stimulation of a chemoreceptor. In another embodiment of the methods of the present invention, the molecules are hormones. In another embodiment of the methods of the present invention, the molecules are selected from one or more of the group consisting of cholecystokinin, peptide $YY_{3-36}$, glucagon-like peptide 1, gastric-inhibitory peptide, neurotensin, amylin, leptin, bombesin, calcitonin, calcitonin gene-related peptide, somatostatin, neuromedin U and glucagon.

In another embodiment of the methods of the present invention, the molecules activate a receptor in the periphery to cause a subsequent physiological effect. In another embodiment of the methods of the present invention, the molecules activate a receptor in the liver to cause a subsequent physiological effect. In another embodiment of the methods of the present invention, the molecules activate a receptor in the pylorus to cause a subsequent physiological effect. In another embodiment of the methods of the present invention, the molecules activate a receptor in the brain to cause a subsequent physiological effect.

In another embodiment of the methods of the present invention, the elongated member comprises at least one angle that matches an angle of said organism's small intestine. In another embodiment of the methods of the present invention, the elongated member further comprises an angle of about 70°. In another embodiment of the methods of the present invention, the elongated member further comprises an angle of about 70°. In another embodiment of the methods of the present invention, the elongated member further comprises an angle of about 71°. In another embodiment of the methods of the present invention, the elongated member further comprises an angle of about 72°. In another embodiment of the methods of the present invention, the elongated member further comprises an angle of about 73°. In another embodiment of the methods of the present invention, the elongated member further comprises an angle of about 74°. In another embodiment of the methods of the present invention, the elongated member further comprises an angle of about 75°. In another embodiment of the methods of the present invention, the elongated member further comprises an angle of about 76°. In another embodiment of the methods of the present invention, the elongated member further comprises an angle of about 77°. In another embodiment of the methods of the present invention, the elongated member further comprises an angle of about 78°. In another embodiment of the methods of the present invention, the elongated member further comprises an angle of about 79°. In another embodiment of the methods of the present invention, the elongated member further comprises an angle of about 80°. In another embodiment of the methods of the present invention, the elongated member further comprises an angle of about 81°. In another embodiment of the methods of the present invention, the elongated member further comprises an angle of about 82°. In another embodiment of the methods of the present invention, the elongated member further comprises an angle of about 83°. In another embodiment of the methods of the present invention, the elongated member further comprises an angle of about 84°. In another embodiment of the methods of the present invention, the elongated member further comprises an angle of about 85°. In another embodiment of the methods of the present invention, the elongated member further comprises an angle of about 86°. In another embodiment of the methods of the present invention, the elongated member further comprises an angle of about 87°. In another embodiment of the methods of the present invention, the elongated member further comprises an angle of about 88°. In another embodiment of the methods of the present invention, the elongated member further comprises an angle of about 89°. In another embodiment of the methods of the present invention, the elongated member further comprises an angle of about 90°. In another embodiment of the methods of the present invention, the elongated member comprises two angles, each matching an angle of said organism's small intestine.

DETAILED DESCRIPTION

Figure 1:
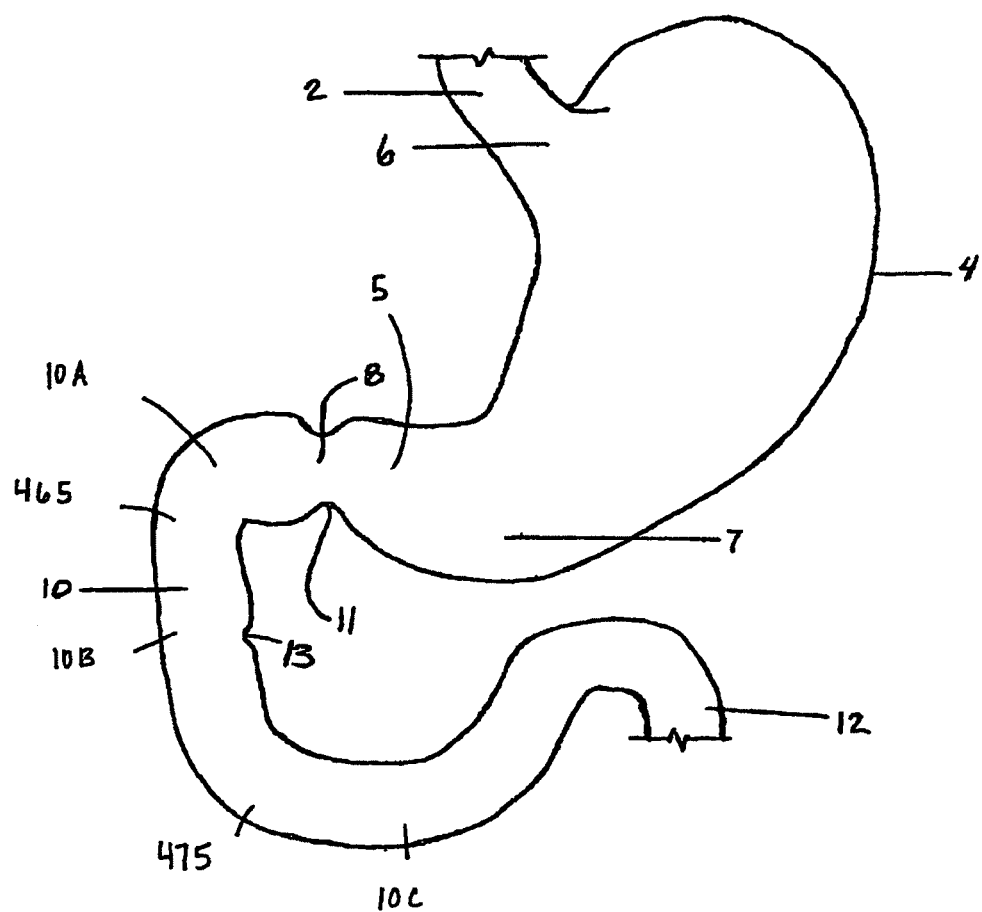
FIG. 1 is a general thawing of the stomach and duodenum of the small intestine.

It is to be understood that the present invention is not limited to the particular embodiments, materials, and examples described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a flow reduction element" or "a satiety signal" is a reference to one or more flow reduction elements or satiety signals and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The phrases "satiety signal(s)" and "signal(s) of satiety" include any biological occurrence that contributes to a feeling of fullness and/or the cessation, slowing or reduction of food intake. Generally, satiety signals are initiated or begin through vagal afferent nerve signals and/or through the arrival at the brain of hormones or other molecules that are released (either directly or indirectly) in response to digestive occurrences. When these vagal afferent nerve signals and/or hormones or other molecules arrive at the brain, they can trigger numerous different neural pathways that contribute to a feeling of fullness and/or the cessation, slowing or reduction of food intake. The phrases "satiety signal(s)" and "signal(s) of satiety" are meant to include both the origination of these signals in the periphery and their integration within the central nervous system which can ultimately affect behavior.

The phrase "activate a receptor" includes that a molecule comes into close enough contact with a receptor to induce a physiological change in the receptor or that an event such as mechanical deformation or stretch induces a physiological change in a receptor.

The phrase "activate a receptor . . . to cause a physiological effect" includes that a molecule has come into close enough contact with a receptor to induce a physiological change in the receptor or that an event such as mechanical deformation or stretch induces a physiological change in a receptor such that one of a number of physiological events occurs. For example, the change can cause an effect such as the release of a molecule from the receptor's cell, the opening or closing of an ion channel or an increase or decrease in the activity of a g-protein, kinase or cellular enzyme. The effect can be an increase or a decrease in the transcription of a gene. The effect can also be to make another physiological effect more or less likely to occur given the existence of other physiological events. For example, the effect can be to make the opening or closing of an ion channel more or less likely based on the reactivation of the same receptor or the activation of a different receptor. The effect also can be the firing of an afferent nerve fiber or the making of the firing of an afferent nerve fiber more or less likely. All of these physiological effects can either serve to create satiety signals or can lead to additional downstream effects, such as protein formation and/or release that can serve to create satiety signals.

The term "bioactive material(s)" refers to any organic, inorganic, or living agent that is biologically active or relevant. For example, a bioactive material can be a protein, a polypeptide, a polysaccharide (e.g. heparin), an oligosaccharide, a mono- or disaccharide, an organic compound, an organometallic compound, or an inorganic compound, an antimicrobial agent (including antibacterial and anti-fungal agents), anti-viral agents, anti-tumor agents, immunogenic agents and lipids. It can include a living or senescent cell, bacterium, virus, or part thereof. It can include a biologically active molecule such as a hormone, a growth factor, a growth factor-producing virus, a growth factor inhibitor, a growth factor receptor, an anti-inflammatory agent, an antimetabolite, an integrin blocker, or a complete or partial functional insense or antisense gene. It can also include a man-made particle or material, which carries a biologically relevant or active material. An example is a nanoparticle comprising a core with a drug and a coating on the core. A bioactive material also can be a by-product of digestion or an agent that alters the pH of its surrounding environment.

Bioactive materials also can include drugs such as chemical or biological compounds that can have a therapeutic effect on a biological organism. Bioactive materials include those that are especially useful for long-term therapy such as hormonal treatment. Examples include drugs for suppressing appetite, contraception and hormone replacement therapy, and for the treatment of diseases such as osteoporosis, cancer, epilepsy, Parkinson's disease and pain. Suitable bioactive materials can include, without limitation, analgesics and analgesic combinations, antiasthmatic agents, anticonvulsants, antidepressants, antidiabetic agents, antineoplastics, antipsychotics, and agents used for cardiovascular diseases such as anti-coagulant compounds.

Bioactive materials also can include precursor materials that exhibit the relevant biological activity after being metabolized, broken-down (e.g. cleaving molecular components), or otherwise processed and modified within the body. These can include such precursor materials that might otherwise be considered relatively biologically inert or otherwise not effective for a particular result related to the medical condition to be treated prior to such modification.

Combinations, blends, or other preparations of any of the foregoing examples can be made and still be considered bioactive materials within the intended meaning herein. Aspects of the present invention directed toward bioactive materials can include any or all of the foregoing examples.

Non-limiting examples of bioactive materials that can be included with the present invention include satiety promoting signals such as cholecystokinin, peptide $YY_{3-36}$, glucagon-like peptide 1, gastric-inhibitory peptide, neurotensin, amylin, leptin, bombesin, calcitonin, calcitonin gene-related peptide, somatostatin, neuromedin U and glucagon. Other non-limiting examples of bioactive materials that can be included in accordance with the present invention include proteins or peptides including, without limitation, albumin, atrial natriuretic factor, renin, superoxide dismutase, α$_1$-antitrypsin, bacitracin, bestatin, cyclosporine, delta sleep-inducing peptide (DSIP), endorphins, gramicidin, melanocyte inhibiting factors, oxytocin, terprotide, serum thymide factor, thymosin, antidiuretic hormones such as DDAVP, dermorphin, Met-enkephalin, peptidoglycan, satietin, thymopentin, fibrin degradation product, des-enkephalin-α-endorphin, gonadotropin releasing hormone, leuprolide, α-MSH, and metkephamid.

Bioactive materials of the present invention also can include, without limitation, naturally-occurring or synthesized hormones. Non-limiting examples of such hormones include corticosteroids including mineralocorticosteroids (including, without limitation cortisol, deoxycorticosterone and fluorohydrocortisone) and glucocorticoids (including beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide)). Androgenic steroids, such as without limitation, danazole, fluoxymesterone, mesterolone, methyltestosterone, testosterone and salts thereof can also be included. Anabolic steroids, such as without limitation, calusterone, nandrolone and salts thereof, dromostanolone, oxandrolone, ethylestrenol, oxymetholone, methandriol, stanozolol methandrostenolone, testolactone can also can be included. Antiandrogen steroids, such as without limitation, cyproterone acetate can also be included. Estrogens including diethylstilbestrol, estradiol, estriol, ethinylestradiol, mestranol, and quinestrol as well as anti-estrogens, such as chlorotrianisene, clomiphene, ethamoxytriphetol, nafoxidine, tamoxifen can be included.

Bioactive materials of the present invention also include, without limitation, progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

The following non-limiting bioactive materials can also be used in accordance with the present invention:

Anti-tumor agents: altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin;

Antimicrobial Agents

1. Antibiotics: Penicillins: ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin;

2. Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, cephalexin;

3. Aminoglycosides: amikacin, neomycin, dibekacyn, kanamycin, gentamycin, netilmycin, kanamycin, tobramycin;

4. Macrolides: amphotericin B, novobiocin, bacitracin, nystatin, clindamycin, polymyxins, colistin, rovamycin, erythromycin, spectinomycin, lincomycin, vancomycin;

5. Tetracyclines: chlortetracycline, oxytetracycline, demeclocycline, rolitetracycline, doxycycline, tetracycline, minocycline;

6. Other antibiotics: chloramphenicol, rifamycin, rifampicin, thiamphenicol;

Chemotherapeutic Agents:

1. Sulfonamides: sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole, trimethoprim with sulfamethoxazole or sulfametrole;

2. Urinary tract antiseptics: methanamine, quinolones (norfloxacin, cinoxacin), nalidixic acid, nitro-compounds (nitrofurantoin, nifurtoinol), oxolinic acid;

3. Anaerobic infections: metronidazole;

Drugs for tuberculosis: aminosalicyclic acid, isoniazide, cycloserine, rifampicine, ethambutol, tiocarlide, ethionamide, viomycin;

Drugs for leprosy: amithiozone, rifampicine, clofazimine, sodium sulfoxone, diaminodiphenylsulfone (DDS, dapsone);

Antifungal agents: amphotericin B, ketoconazole, clotrimazole, miconazole, econazole, natamycin, flucytosine, nystatin, griseofulvin;

Antiuiral agents: aciclovir, idoxuridine, amantidine, methisazone, cytarabine, vidarabine, ganciclovir;

Chemotherapy of amebiasis: chloroquine, iodoquinol, clioquinol, metronidazole, dehydroemetine, paromomycin, diloxanide, furoatetinidazole, emetine;

Anti-malarial agents: chloroquine, pyrimethamine, hydroxychloroquine, quinine, mefloquine, sulfadoxine/pyrimethamine, pentamidine, sodium suramin, primaquine, trimethoprim, proguanil;

Anti-helminthiasis agents: antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole, niclosamide;

Anti-inflammatory agents: acetylsalicylic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen, tolmetin Anti-gout agents: colchicine, allopurinol;

Centrally acting (opioid) analgesics: alfentanil, methadone, bezitramide, morphine, buprenorfine, nicomorphine, butorfanol, pentazocine, codeine, pethidine, dextromoramide, piritranide, dextropropoxyphene, sufentanil, fentanyl Local anesthetics: articaine, mepivacaine, bupivacaine, prilocalne, etidocaine, procaine, lidocaine, tetracaine;

Drugs for Parkinson's disease: amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide, trihexyphenidyl;

Centrally active muscle relaxants: baclofen, carisoprodol, chlormezanone, chlorzoxazone, cyclobenzaprine, dantrolene, diazepam, febarbamate, mefenoxalone, mephenesin, metoxalone, methocarbamol, tolperisone;

Thyroid Drugs

1. Thyroid drugs used in therapy: levothyronine, liothyronine;

2. Anti-thyroid drugs used in therapy: carbimazole, methimazole, methylthiouracil, propylthiouracil;

Viral surface antigens or parts of viruses: adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses, Yellow Fever Virus;

Bacterial surface antigens or parts of bacteria: *Bordetella pertussis, Helicobacter pylom, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera, Yersinia pestis;*

Surface antigens of parasites causing disease or portions of parasites:

*Plasmodium vivax*—malaria, *Plasmodium falciparum*—malaria, *Plasmodium ovale*—malaria, *Plasmodium malariae*—malaria, *Leishmania tropica*—leishmaniasis, *Leishmania donovani*, leishmaniasis, *Leishmania branziliensis*—leishmaniasis, *Trypanosoma rhodescense*—sleeping sickness, *Trypanosoma gambiense*—sleeping sickness, *Trypanosoma cruzi*—Chagas' disease, *Schistosoma mansoni*—schistosomiasis, *Schistosomoma haematobium*—schistomiasis, *Schistosoma japonicum*—shichtomiasis, *Trichinella spiralis*—trichinosis, *Stronglyloides duodenale*—hookworm, *Ancyclostoma duodenale*—hookworm, *Necator americanus*—hookworm, *Wucheria bancroftii*—filariasis, *Brugia malaya*—filariasis, *Loa loa*—filariasis, *Dipetalonema perstaris*—filariasis, *Dracuncula medinensis*—filariasis, *Onchocerca volvulus*—filariasis;

Immunoglobulins: IgG, IgA, IgM, Antirabies immunoglobulin, Antivaccinia immunoglobulin;

Antitoxins: Botulinum antitoxin, diphtheria antitoxin, gas gangrene antitoxin, tetanus antitoxin; and Antigens which elicit an immune response against: Foot and Mouth Disease, hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.

FIG. 1 shows the human stomach 4 and duodenum of the small intestine 10. Important features are the esophagus 2, stomach 4, antrum 7, pylorus 8, pyloric valve 11, duodenum 10, jejunum 12 and ampulla of Vater 13. Functionally, the esophagus 2 begins at the nose or mouth at its superior end and ends at the stomach 4 at its inferior end. The stomach 4 encloses a chamber which is characterized, in part, by the esophageal-gastric juncture 6 (an opening for the esophagus 2) and the antrum-pyloric juncture 5 (a passageway between the antrum 7 through the pylorus 8 to the duodenum 10 of the small intestine). The pylorus 8 controls the discharge of contents of the stomach 4 through a sphincter muscle, the pyloric valve 11, which allows the pylorus 8 to open wide enough to pass sufficiently-digested stomach contents (i.e., objects of about one cubic centimeter or less). These gastric contents, after passing into the duodenum 10, continue into the jejunum 12 and on into the ileum (not shown). The duodenum 10, jejunum 12 and ileum make up what is known as the small intestine. However these individual portions of the alimentary canal are sometimes individually referred to as the small intestine. In the context of this invention the small intestine can refer to all or part of the duodenum, jejunum and/or ileum. The ampulla of Vater 13, which provides bile and pancreatic fluids that aid in digestion is shown as a small protrusion on the medial wall of the duodenum 10.

The adult duodenum, described as having four parts, is about 20-25 cm long and is the shortest, widest, and most predictably placed part of the small intestine. The duodenum forms an elongated 'C' that lies between the level of the first and third lumbar vertebrae in the supine position. Susan Standring (ed.), GRAY's ANATOMY, 39$^{th}$ Ed., 1163-64 (2005).

The first part of the duodenum, often referred to as the duodenal bulb 460, is about 5 cm long and starts as a continuation of the duodenal end of the pylorus 8. This first part of the duodenum passes superiorly, posteriorly and laterally for 5 cm before curving sharply inferiorly into the superior duodenal flexure 465, which marks the end of the first part of the duodenum. Id. The second part of the duodenum, often called the vertical duodenum 470, is about 8-10 cm long. It starts at the superior duodenal flexure 465 and runs inferiorly in a gentle curve towards the third lumbar vertebral body. Here, it turns sharply medially into the inferior duodenal flexure 475 which marks its junction with the third part of the duodenum. Id. The third part of the duodenum, often called the horizontal duodenum 480, starts at the inferior duodenal flexure and is about 10 cm long. It runs from the right side of the lower border of the third lumbar vertebra, angled slightly superiorly, across to the left and ends in continuity with the fourth part of the duodenum in front of the abdominal aorta. Id. The fourth part of the duodenum is about 2.5 cm long. It starts just to the left of the aorta and runs superiorly and laterally to the level of the upper border of the second lumbar vertebra. It then turns antero-inferiorly at the duodenojejunal flexure and is continuous with the jejunum. Id. Some embodiments of the present invention take advantage of this predictable configuration of the small intestine to provide duodenal/small intestinal implants that do not require anchoring within the pylorus or stomach (described more fully infra).

The digestive process starts when consumed foods are mixed with saliva and enzymes in the mouth. Once food is swallowed, digestion continues in the esophagus and in the stomach, where the food is combined with acids and additional enzymes to liquefy it. The food resides in the stomach for a time and then passes into the duodenum of the small intestine to be intermixed with bile and pancreatic juice. Mixture of the consumed food with bile and pancreatic juice makes the nutrients contained therein available for absorption by the villi and microvilli of the small intestine and by other absorptive organs of the body.

The presence of partially digested food within the stomach and small intestine begins a cascade of biological signals that create satiety signals and contribute to the cessation of food intake. One such satiety signal is initiated by the release of cholecystokinin ("CCK"). Cells of the small intestine release CCK in response to the presence of digested foods, and in particular, without limitation, in response to dietary fat, fatty acids, small peptides released during protein digestion and amino acids. Wynne et al., 184 J. ENDOCRIN. 291-318 (2005); Havel, 226 SOC'Y FOR EXP. BIOL. AND MED. 963-977 (2001). Once released in response to these dietary signals, CCK remains elevated for about 5 hours. Liddle et al., 75 J. CLIN. INV. 1144-1152 (1985). Elevated levels of CCK reduce meal size and duration and may do so through a number of different mechanisms. Gibbs et al., 84 J. COMP. PHYSIOL. AND PSYCH. 488-95 (1973); Kissileff et al., 285 AM. J. OF PHYSIOL—REG., INT. AND COMP. PHYSIOL.

R992-98 (2003). For example, CCK may act on CCK-A receptors in the liver and within the central nervous system to induce satiety signals. CCK stimulates vagal afferent fibers in both the liver and the pylorus that project to the nucleus tractus solitarius (NTS), an area of the brain that communicates with the hypothalamus to centrally regulate food intake and feeding behavior. CCK also stimulates the release of enzymes from the pancreas and gall bladder and inhibits gastric emptying. Liddle et al., supra; Moran & Schwarz, 9 CRIT. REV. 1N NEUROBIOL. 1-28 (1994). Because CCK is a potent inhibitor of gastric emptying, some of its effects on limiting food intake may be mediated by the retention of food in the stomach. Wynne et al., supra; Havel, supra.

Cells of the small intestine (particularly L cells) also release glucagon-like peptide 1 (GLP-1) and oxyntomodulin (OXM) in response to nutrient signals of digestion. Hermann et al., 56 DIGESTION 117-26 (1995); Ghatei et al., 57 J. CLIN. ENDOCRINOL. AND METAB. 488-95 (1983); Le Quellec et al., 74 J. CLIN. ENDOCRINOL. AND METAB. 1405-09 (1992). Elevated levels of GLP-1 and OXM are associated with satiety signals and the cessation of food intake. Elevated OXM levels, specifically, have been shown to reduce hunger and to decrease caloric intake by about 10% for about 12 hours. Cohen et al., 88 J. CLIN. ENDOCRINOL. AND METAB. 4696-701 (2003). These signals could signal satiety by activating receptors on afferent vagal nerves in the liver and/or the GI tract and/or by inhibiting gastric emptying. Naslund et al., 277 AM. J. OF PHYSIOL—REG., INT. AND COMP. PHYSIOL. R910-16 (1999); Schirra et al., 156 J. ENDOCRINOL. 177-186 (1998).

Pancreatic peptide (PP) is released in proportion to the number of calories ingested. Circulating levels of PP also have been shown to be increased by gastric distension. Elevated levels of PP have been shown to reduce food intake and body weight. Malaisse-Lagae et al., 33 EXPERIENTIA 915-17 (1977); Asakawa et al., 124 GASTROENTEROL. 1325-36 (2003). Humans given an infusion of PP demonstrate decreased appetite and an about 25% reduction in food intake for about 24 hours following the infusion. Batterham et al., 88 J. CLIN. ENDOCRINOL. AND METAB. 3989-92 (2003). PP may exert some of its anorectic effects via vagal afferent pathways to the brainstem. Asakawa et al., supra. PP also may reduce food intake through its suppression of gastric ghrelin mRNA expression.

Peptide $YY_{3-36}$ ($PYY_{3-36}$) is another biological signal whose peripheral release may be correlated with reduced food intake and/or the cessation of eating. Specifically, low levels of $PYY_{3-36}$ have been correlated with obesity while its administration decreases caloric intake and subjective hunger scores. Batterham et al., supra. Indeed, intravenous (i.v.) administration of $PYY_{3-36}$ can reduce food intake by about 30% for up to about 12 hours. Batterham et al., 349 NEW ENGLAND J. MED. 941-48 (2003); Batterham et al., 418 NATURE 650-54 (2002). $PYY_{3-36}$ may reduce food intake through its effects of suppressing ghrelin expression, delaying gastric emptying, delaying various secretion from the pancreas and stomach and increasing the absorption of fluids and electrolytes from the ileum after a meal.

Insulin and leptin are two additional biological signals that regulate satiety and eating behavior. Through parasympathetic innervation, β cells of the endocrine pancreas release insulin in response to circulating nutrients such as, without limitation, glucose and amino acids, and in response to the presence of GLP-1 and gastric inhibitory peptide (GIP). Havel, supra. Insulin stimulates leptin production from adipose tissue via increased glucose metabolism.

Increased insulin levels in the brain lead to a reduction in food intake. Elevated leptin levels also decrease food intake and induce weight loss. Caro et al., 45 DIABETES 1455-62 (1996); Havel, 59 PROC. NUTR. SOC. 359-71 (2000). Insulin and leptin have also been implicated in the regulation of energy expenditure since their administration induces greater weight loss than can be explained by reduction in food intake alone. Levin et al., 93 PROC. NATL. ACAD. SCI. 1726-30 (1996); Scarpace et al., 273 AM. J. PHYSIOL. E226-E230 (1997); Collins et al., 380 NATURE 677 (1996); Haynes et al., 100 J. CLIN. INVEST. 270-78 (1997).

Both insulin and leptin act within the central nervous system to inhibit food intake and to increase energy expenditure, most likely by activating the sympathetic nervous system. Collins et al, supra; Haynes et al., supra. Insulin's effects to decrease food intake also involve interactions with several hypothalamic neuropeptides that are also involved in the regulation of feeding behavior such as, without limitation, NPY and melanocortin ligands. Schwartz et al., 404 NATURE 661-671 (2000); Schwartz et al., 69 AM. J. CLIN. NUTR. 584-596 (1999); Collins et al., supra; Haynes et al., supra.

Other hormones or biological signals that are involved in the suppression or inhibition of food intake include, without limitation, GIP (secreted from intestinal endocrine K cells after glucose administration or ingestion of high carbohydrate meals; D'Alessio et al., 86 J. CLIN. ENDOCRINOL. METAB. 1253-59 (2001); enterostatin (produced in response to dietary fat; Havel, supra), amylin (co-secreted with insulin from pancreatic β cells); glucagon, gastrin-releasing peptide (GRP), somatostatin, neurotensin, bombesin, calcitonin, calcitonin gene-related peptide, neuromedin U (NMU) and ketones.

In relation to the present invention, if the passage of partially digested food as described is partially blocked within the duodenum of the small intestine and the flow rate through this area is reduced, the emptying of the stomach and the duodenum will occur more slowly. This slowing, by itself, may create extended feelings of satiety and thus lead to a decrease in food intake (due to the retention of food in the stomach for a longer period of time). The slowing of the passage of food also provides a greater amount of time for the partially digested food to interact with chemoreceptors, stretch receptors and mechanoreceptors along the GI tract so that stimulation of satiety signals may be increased and/or prolonged. For example, increased and/or prolonged satiety signals may lead to a reduction in food intake by leading to a shorter duration of food intake and/or longer periods between food intake.

In addition to keeping partially-digested food within the small intestine for an extended period of time, the methods and devices of the present invention also can enhance and/or prolong the release and/or occurrence of satiety signals by releasing signals into the small intestine themselves. For example, in one embodiment, the methods and devices of the present invention can release nutrient products of digestion to stimulate chemoreceptors to cause the release of hormones and/or other molecular signals that contribute to the creation of satiety signals. In another embodiment, the methods and devices of the present invention may exert a small amount of pressure on the walls of the GI tract to stimulate stretch and/or mechanoreceptors to generate and send satiety signals to the brain. In another embodiment, the methods and devices of the present invention can release signals, such as, without limitation nutrient by-products of digestion of food, to stimulate chemoreceptors as described above and can exert a small amount of pressure on the walls of the small intestine as described above to contribute to the generation of satiety signals.

The methods and devices of the present invention may also contribute to weight loss and the treatment of obesity by covering portions of the walls of the small intestine, thus blocking some nutrient uptake and/or interrupting or reducing the intermixing of the digestive fluids. In one embodiment, the methods and devices of the present invention may further include a central tube which funnels a portion of the consumed food through the small intestine without being fully digested or absorbed. In these manners, the methods and devices of the present invention can inhibit the absorption of partially digested food materials. The partially digested food materials are then passed to the large intestine for elimination with limited caloric absorption by the body.

Figure 2:
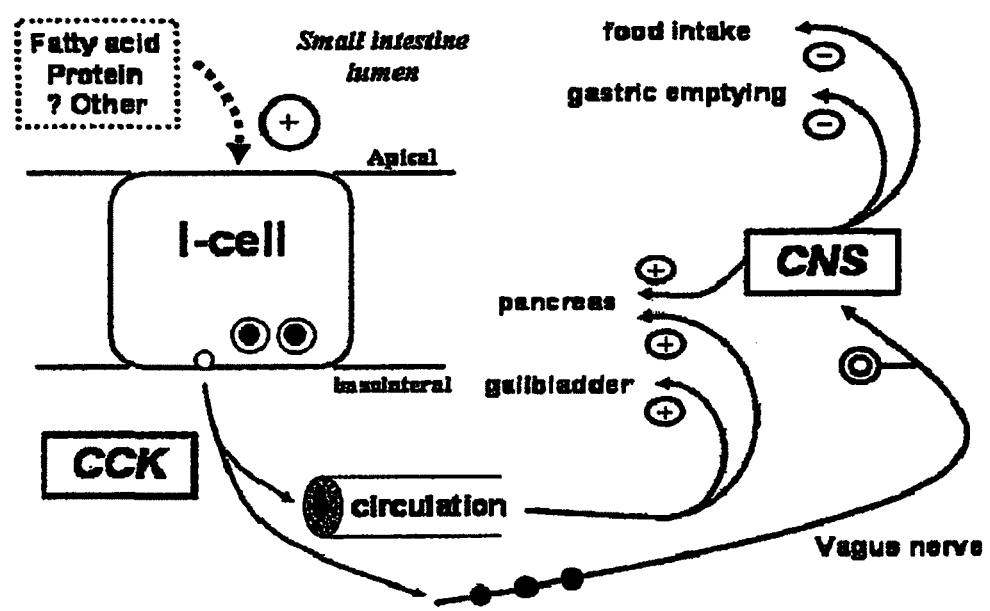
FIG. 2 depicts several exemplary mechanisms through which satiety signals may be generated.

FIG. 2 depicts several exemplary non-limiting mechanisms through which satiety signals may be generated. In this FIG. 2, a by-product of digestion, such as a fatty acid or other protein, stimulates an L-cell of the small intestine to release CCK locally and into the circulation. CCK released locally can stimulate vagal afferent nerve fibers in the area to generate satiety signals to the central nervous system (CNS). CCK that enters the circulation can travel to the liver to, without limitation, stimulate vagal afferent nerve fibers in the liver to generate satiety signals to the CNS. CCK in the circulation can travel to the gall bladder and pancreas to upregulate the digestion-related activities of these organs. CCK in the circulation also can travel to the CNS itself to contribute to the creation of a satiety signal. Once satiety signals are received and integrated within the CNS, the CNS can trigger physiological effects that serve to contribute to a feeling of fullness and/or the cessation, slowing or reduction of food intake.

Figure 3:
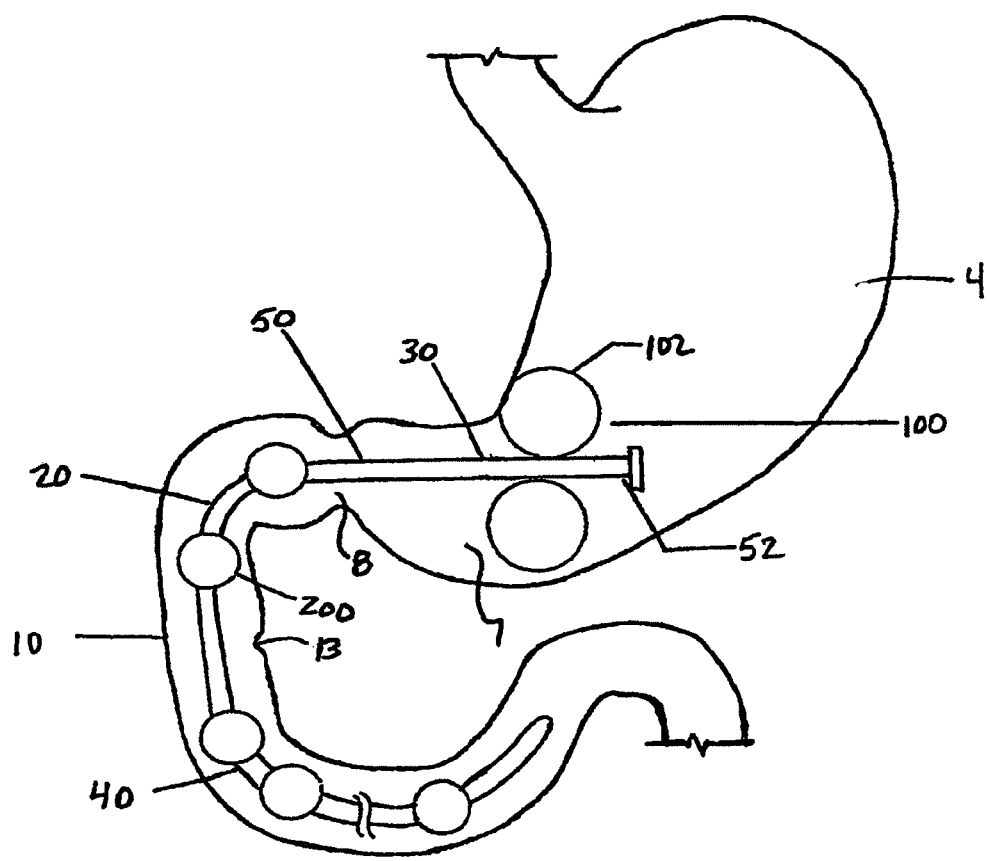
FIG. 3 is a perspective view of one embodiment of a duodenal/small intestinal insert in accordance with the present invention positioned inside the stomach and small intestine.

FIG. 3 shows one exemplary non-limiting small intestinal insert 20 made in accordance with the present invention that can contribute to the creation of satiety signals. The insert 20 is positioned in the stomach 4 and small intestine 10. The insert 20 has a proximal portion 30 and a distal portion 40, and a central tube 50 that extends from the proximal portion 30 to the distal portion 40. One or more flow reduction elements 200 that are sized to fit within the small intestine 10 can be attached to the central tube 50. While not required, the portion of the central tube 50 near the ampulla of Vater 13 generally will not include a flow reduction element 200 so that the introduction of bile and pancreatic fluid into the small intestine is not impeded.

In one embodiment, the central tube 50 has an anchoring member 100 near its proximal end 52, with the anchoring member 100 securing the proximal end 52 of the central tube 50 in the antrum 7 of the stomach. The anchoring member 100 is sized so that it will not pass through the pylorus 8. In this way, embodiments of the present invention including an anchoring member anchor the flow reduction elements 200 within the small intestine. In one embodiment, the anchoring member can be established by one or more inflatable balloons 102 that when inflated are larger than the pylorus 8. The inflatable balloons 102 can be deflated for delivery into the stomach and then inflated inside the stomach. The inflatable balloons 102 can also be deflated for later removal using endoscopic techniques.

The length of the central tube 50 can be established depending on the therapeutic result desired. For example, the central tube 50 and the one or more attached flow reduction elements 200 may extend into a portion of or through the entire duodenum 10. On some patients the central tube 50 and the one or more attached flow reduction elements 200 may extend past the duodenum 10 and into the jejunum 12. It is anticipated that differing lengths of central tubes and differing numbers and configurations of the flow reduction elements can be used by a physician to treat various body types and metabolic demands. In one example, if a patient is 20% overweight, a physician might select a length of central tube 50 with attached flow reduction elements 200 that permit absorption of only 80% of the nutritional potential of a typical daily intake of calories. This reduction of caloric intake over time could lead to an appropriate amount of weight loss in the patient.

Figure 4:
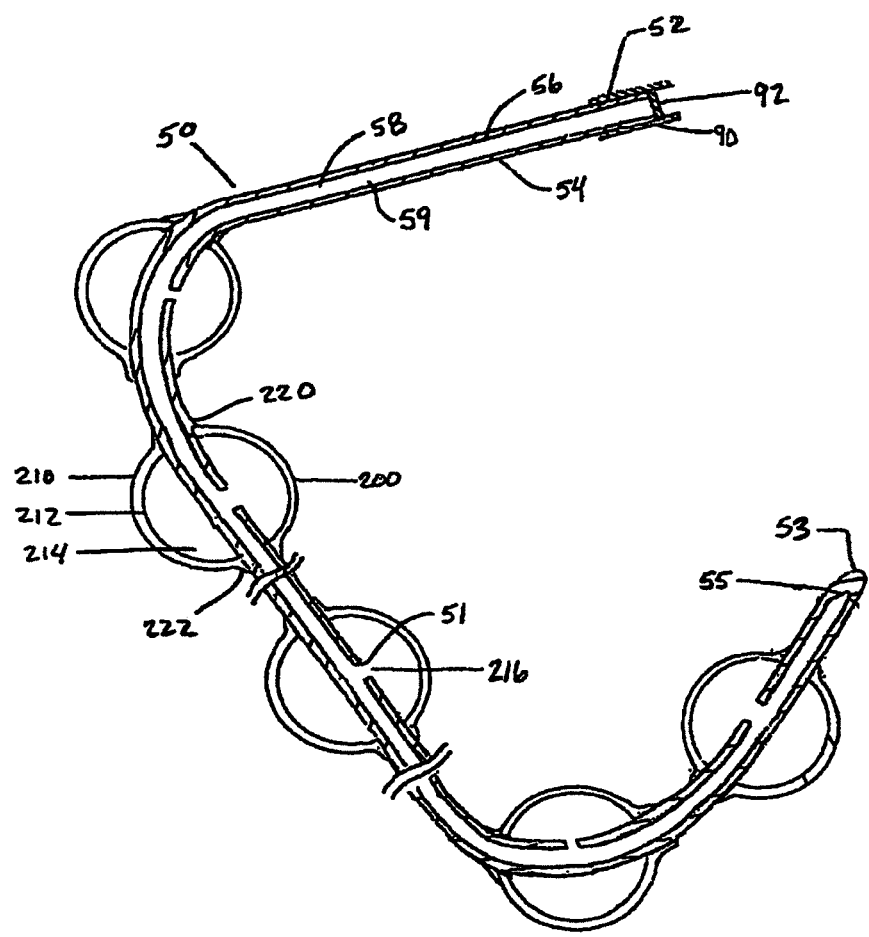
FIG. 4 is a partial section view of a central tube illustrating attached flow reduction elements and a central lumen.

FIG. 4 shows one embodiment of a central tube 50 with an outer wall 54 and an inner wall 56 that define an interior space 58. The interior space 58 forms an inner lumen 59 that may be continuous from the proximal end 52 of the central tube 50 to just short of the distal end 53 of the central tube 50. The distal end 53 of the central tube 50 is sealed at a point 55 so that fluid introduced into the central tube 50 does not leak out distally into the small intestine. In some embodiments a valve 90 can be located substantially at the proximal end of the inner lumen 59. The valve 90 may be a self sealing valve that has a septum 92 that can be accessed by a needle or blunt tip tube for introduction of fluid into the inner lumen 59. The valve 90 also can be accessed so that the fluid inside the inner lumen 59 of the central tube 50 can be aspirated for removal. It is to be understood that the valve type is not limited to a septum type valve only, and that other types of mechanical valves may also be used in place of the septum valve described. Particular embodiments of the present invention are adapted to accept fluids in this manner so that the devices of the present invention can be implanted in a deflated configuration and later expanded into an inflated configuration.

As shown in FIG. 4 and as mentioned above, one or more flow reduction elements 200 can be attached to the central tube 50. In some embodiments the diameter of each flow reduction element 200 can be concentric with the axis of the central tube 50. In the embodiment depicted in FIG. 4, each flow reduction element 200 has an outer wall 210, an inner wall 212, and an inner space 214. At or near its proximally-oriented surface 220 and also at or near its distally-oriented surface 222, each flow reduction element 200 can be attached to the central tube 50 with the inner space 214 of the flow reduction element 200 in fluid communication with the lumen 59 of the central tube 50, such that the inner space 214 surrounds the outer wall 54 of the central tube 50. Each flow reduction element 200 may be attached to the central tube 50 by, without limitation, adhesives, heat bonding, mechanical restraint or other suitable methods.

As also depicted in FIG. 4, the central tube 50 can be formed with plural inlet/exit ports 216 that are located inside respective flow reduction elements 200. More specifically, each port 216 is formed completely through the central tube wall 51 to establish a pathway for fluid communication between the inner lumen 59 of the central tube 50 and the inner space 214 of the respective flow reduction elements 200. Consequently, the inner lumen 59 of the central tube 50 may be used to introduce fluid into the inner spaces 214 of the flow reduction elements 200 and to inflate the flow reduction elements 200 from a collapsed configuration, in which insertion and removal of the flow reduction elements 200 is facilitated, to an inflated configuration shown in FIG. 4, in which resistance to food passage is increased to induce satiety. Thus, as suggested earlier, the flow reduction element or elements 200 in this embodiment act as balloons that can be deflated and collapsed around the central tube 50 for introduction into the small intestine and then inflated to the desired diameter once in position.

In one embodiment, individual flow reduction elements 200 of the present invention can be elastic balloons or inelastic balloons. When an elastic balloon material is used to establish a flow reduction element 200, the flow reduction element 200 inflates to a diameter that is dependent on the volume of fluid introduced into the inner space of the flow reduction element. This embodiment permits adjustment of the balloon size as determined by the physician. If the balloon is too small, for instance, additional fluid could be introduced to enlarge the balloon diameter. Alternatively, if the balloon is too large, additional fluid could be removed to shrink the balloon diameter. It is understood that an alternate embodiment consisting of an inelastic balloon that inflates to a diameter that is independent of a volume of fluid introduced into its inner space is also included within the present invention. The diameter of this type of balloon is fixed when manufactured and does not permit in situ adjustment of the balloon size. However, this type of balloon prevents possible over inflation and rupture if too much fluid is introduced into the balloon.

The flow reduction elements 200 shown in FIG. 4 have the shape of a round sphere. However, other shapes are contemplated and any shape that effectively functions to inhibit the passage of partially digested food in the small intestine is acceptable in accordance with the present invention. It is understood that the ability of the small intestinal insert to remain within the small intestine can be affected by the shape, orientation and tautness of the flow reduction elements 200. For example alternate shapes such as ovoid, elliptical, elongated ellipse and even irregular non-geometrical shapes could be used in accordance with the present invention.

Figure 5:
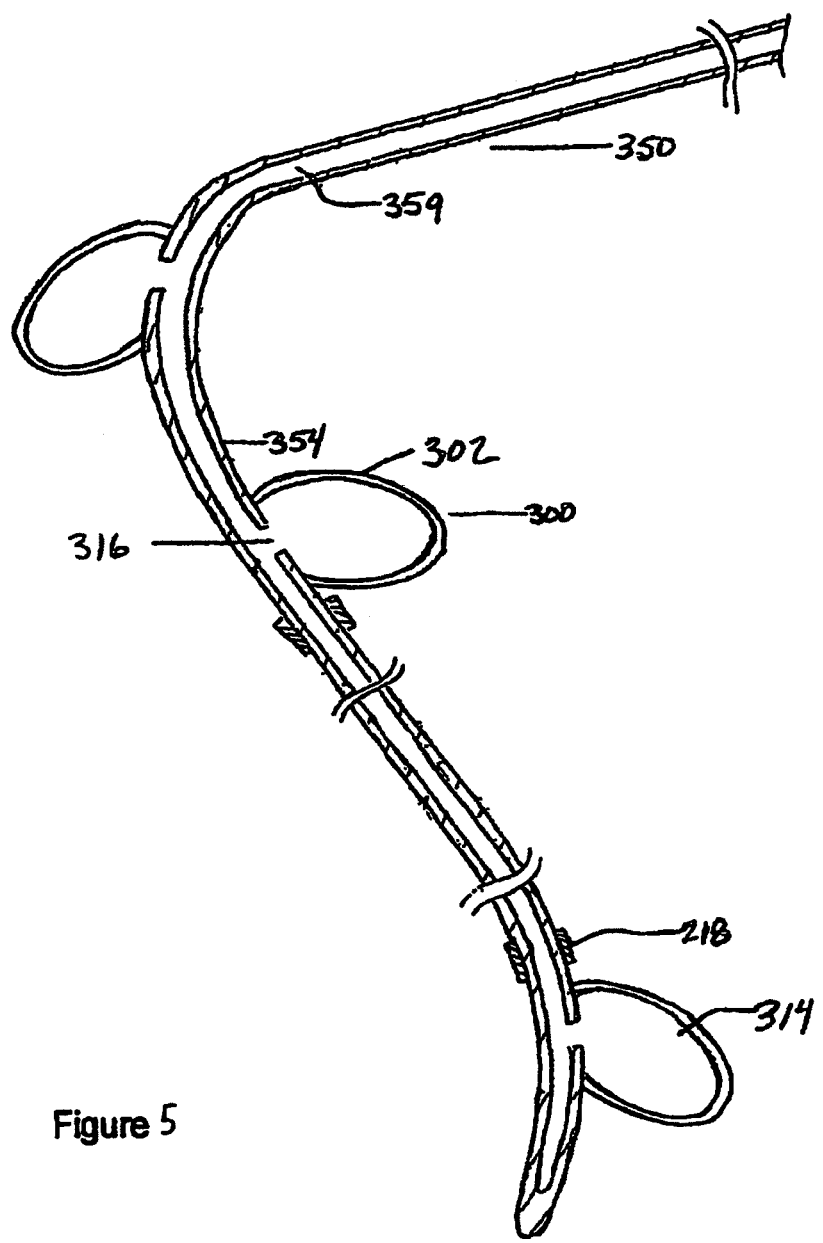
FIG. 5 is a partial section view of a central tube illustrating eccentrically attached flow reduction elements and a central lumen.

FIG. 5 illustrates an alternative embodiment of the present invention in which one or more flow reduction elements 300 are eccentrically attached to a central tube 350. In this embodiment the axis or diameter of the flow reduction element or elements 300 is not concentric with the axis of the central tube. The outer wall 302 of the flow reduction element is attached to the side of an outer wall 354 of the central tube 350. An inner space 314 of each flow reduction element 300 is eccentric relative to the axis of the central tube 350 and is in fluid communication with an inner lumen 359 of the central tube 350 through a respective opening 316. As was the case with the embodiment shown in FIG. 4, in the embodiment shown in FIG. 5 the inner lumen 359 can be used to introduce and remove fluid into the inner space 314 of the flow reduction element 300 to move the flow reduction element 300 between inflated and deflated configurations.

In one embodiment of the present invention, the flow reduction elements 300 can be inflated with a fluid, including a liquid and/or a gas. In one embodiment, the gas can be, without limitation, air, nitrogen or carbon dioxide. In another embodiment a liquid can be, without limitation, water or water mixed with other solutions. Any appropriate inflation medium can be modified to deliver bioactive materials or other signals that can diffuse from the insert of the present invention into the small intestine to trigger biological signals of satiety. When bioactive materials are delivered through an inflation medium, the central tube and/or flow reduction elements should be permeable to the bioactive materials. Porosity can be adjusted to control the diffusion rate of the bioactive materials.

When inflating the flow reduction elements of the present invention, it can be important for the physician to monitor the flow reduction element 300 location in the small intestine and the diameter of the flow reduction element relative to the diameter of the small intestine. For this purpose, the flow reduction element can be inflated with a radiopaque fluid that is visible on X-ray. When the flow reduction element contains radiopaque fluid, a physician can non-invasively visualize the size and placement of the flow reduction element(s) from outside the patient's body. This knowledge enables the physician to adjust the size and/or placement of the flow reduction element(s). Likewise radiopaque marker bands 218 as shown in FIG. 5 can be placed around the central tube to facilitate visualization of the central tube's location in the small intestine. The radiopaque marker bands 218 can be placed at predetermined intervals so that the distance inside the small intestine can be used as depth markers and can be measured from outside of the body.

The central tube and flow reduction elements of the present invention can be flexible. In one embodiment, they can be constructed of a polymeric material that can be easily formed or extruded and delivered with the aid of an endoscope by known techniques. A central tube 50 that is soft and flexible will contour to the anatomy of the gastrointestinal tract and provide less irritation of the stomach and intestinal lining.

Figure 6:
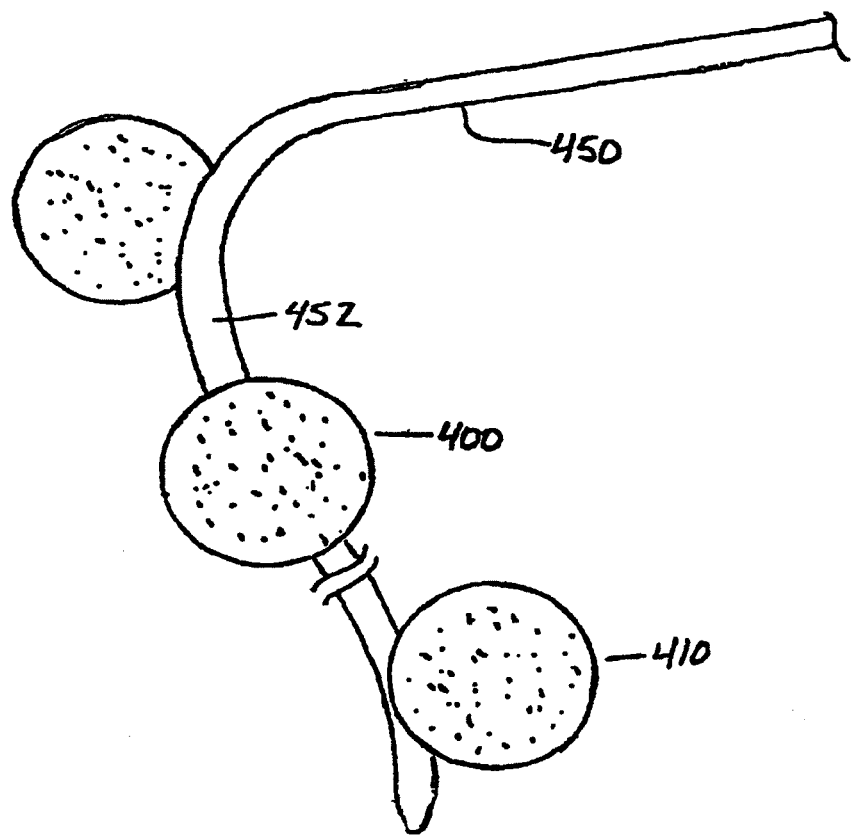
FIG. 6 is a perspective view of an alternative embodiment showing an elongated member and illustrating attached flow reduction elements.

FIG. 6 shows an alternative embodiment of the present invention with a central shaft 450 around which flow reduction elements are concentrically attached 400 and/or are eccentrically attached 410. The elements 400, 410 can be attached to the central shaft 450 by, without limitation, heat fusing, adhesives or other suitable methods as known in the art. These flow reduction elements 400 can be made from material that can be folded or collapsed to a first volume suitable for insertion with the aid of an endoscope and then can self expand to a second volume suitable for restricting the flow of partially digested food according to the present invention. These flow reduction elements can be made from materials such as, without limitation, sponge, foam, hydrogels or springs that can be compacted into a small volume and then self expand to a pre-determined shape and volume when unrestricted. These flow reduction elements may also be impregnated with bioactive materials or other signals that can trigger biological signals of satiety. The central shaft 450 of the embodiment depicted in FIG. 6 can be solid and without an inner lumen or inner space. In another embodiment the central shaft 450 may include a passageway for consumed food so that the food can pass through the small intestine without being fully absorbed. Because the flow reduction elements self expand, the need for an inflation system is eliminated and this embodiment represents a simple mechanical design.

Figure 7:
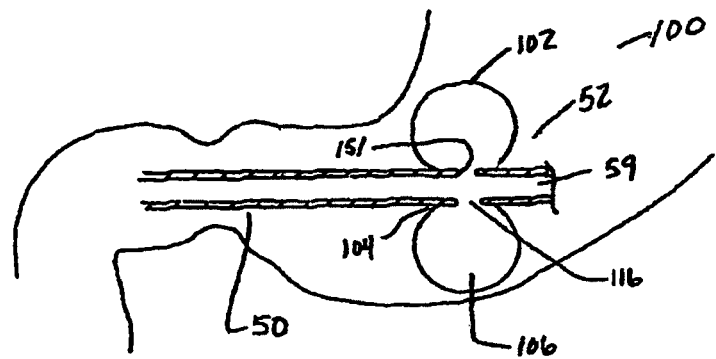
FIG. 7 is a perspective section view of a central tube and an anchoring member.

Turning to various anchoring members that can be used in accordance with the present invention, FIG. 7 depicts one such member. In FIG. 7, the central tube 50 has an anchoring member 100 near its proximal end 52. As stated earlier, the anchoring member 100 can be established by one or more inflatable balloons 102. These balloons 102 can be eccentrically attached to the central tube at point 104 near the proximal end 52 of the central tube 50. These balloons can be formed in many shapes and are not limited to the spherical shape shown. The central tube can be formed with an opening 116 for each respective balloon 102 so that a pathway for fluid communication is established between the inner lumen 59 of the central tube 50 and the inner space of each balloon 106. The inner lumen 59 is used to introduce fluid into the inner space of the balloon 106 and inflate the balloon 102 from a first volume in a collapsed state to a second volume or inflated state.

When the one or more balloons 102 of the anchoring member 100 are fully inflated, they secure the proximal end of the central tube 52 within the antrum of the stomach. The one or more inflatable balloons 102 have a combined cross sectional diameter greater than the diameter of the pyloric valve to prevent migration across the pylorus. The inflatable balloons 102 can be inflated and deflated by adding or removing fluid from the central tube inner lumen 59. The inflatable balloons 102 may be connected to the same central tube inner lumen 59 as the one or more flow reduction elements attached to the central tube and can be inflated simultaneously with the flow reduction elements. The central tube 50 may also have more than one inner lumen so that the inflatable balloons 102 and individual one or more flow reduction elements can be inflated and deflated independently as well.

Figure 8:
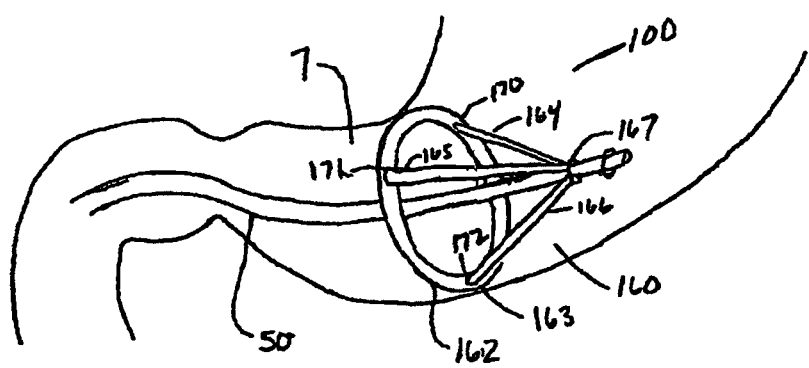
FIG. 8 is a perspective view of an alternative embodiment of a central tube and an anchoring member.

FIG. 8 illustrates another embodiment of an anchoring member 100 of the present invention deployed in the antrum 7. In this embodiment, a central tube 50 is attached to an inverted umbrella skeleton 160. This skeleton 160 has a ring 162 that surrounds the central tube 50 and is supported by struts. In the depicted embodiment the ring 162 is supported by 3 struts 164, 165 and 166, however more or fewer struts can be successfully employed. In the embodiment depicted in FIG. 8, the struts are joined together at the central tube 50 at point 167 and attached to the ring 162 at points 170, 171 and 172. The ring 162 of this anchor configuration can be made from, without limitation, flexible plastic material or flexible wire and has a diameter significantly larger than the diameter of the pyloric valve. This umbrella skeleton 160 can be collapsed around the central tube 50 for insertion into the stomach with the aid of an endoscope. As the device is released from the endoscope, the umbrella skeleton 160 can spring out and assume a configuration similar to that shown in FIG. 8. The struts 164, 165 and 166 may be made from, without limitation, plastic, metal or from plastic covered metal. The edge of the ring which is in contact with the antrum walls 163, may be constructed to assist in securing the umbrella ring 162 to the walls of the antrum. In one embodiment, the surface may be roughened to increase surface friction or the wall may have protrusions or barbs that physically attach to the stomach lining.

Figure 9:
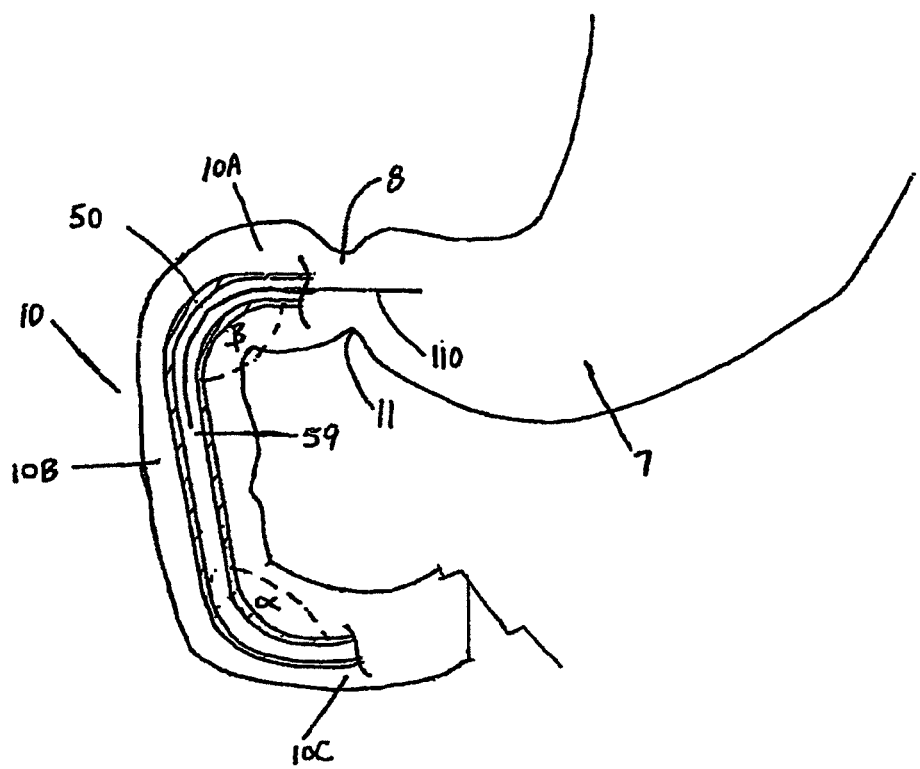
FIG. 9 is a section view of a central tube of the present invention that can lodge in the small intestine for a period of time without any anchoring to the stomach or pylorus.

FIG. 9 shows a central tube 50 of the present invention that may lodge and remain in the small intestine for a period of time without any anchoring to the stomach or pylorus. Embodiments of the present invention that can lodge and remain within the small intestine for a period of time without any anchoring to the stomach or pylorus do so by (i) adopting a central tube with appropriately placed angles that mimic the contours of the small intestine; and (ii) flow reduction elements of an appropriate diameter that help to hold the intestinal insert in place. In one embodiment, while not required, these flow reduction elements can have an abrasive surface or anchoring barbs that can help them adhere to the walls of the small intestine.

In FIG. 9, the first three parts of the duodenum, including the duodenal bulb 10A, the vertical duodenum 10B, and the horizontal duodenum 10C are depicted. The flow reduction elements of the depicted embodiment have been removed for clarity. Distal to the pylorus 8 and immediately after entering the duodenum 10, the central tube 50 can assume a sharp bend of radius β between the duodenal bulb 10A and the vertical duodenum 10B, and a sharp bend of radius a between the vertical duodenum 10B and horizontal duodenum 10C. In one embodiment the radius β and the radius a may be between about 45° and about 110°. In another embodiment the radius β and the radius a may be between about 60° and about 100° such that the central tube 50 bends to follow the inner lumen of the duodenum 10 at these locations that contain predictably configured bends. In another embodiment the radius β and the radius a may be about 80°. While most embodiments of the present invention will include lengths that require adoption of a β and an α angle, shorter devices adopting one or the other are also included within the scope of the present invention. In these described embodiments of the present invention, it can be advantageous that the central tube 50 be flexible enough to conform to the sharp angulations of the small intestine to avoid kinking. One or more flow reduction elements with a diameter about equal to that of the small intestine are also included along the length of the central tube 50. In one embodiment, this diameter is about 3 cm. In another embodiment this diameter is about 4 cm.

The central tube 50 can be pre-formed with a configuration that conforms to the duodenal angulations prior to insertion in the body. This embodiment of the present invention can be constrained in a straight configuration by a stiffening rod 110 placed down the inner lumen 59 of the central tube 50 as shown. This stiffening rod 110 can be placed into a separate lumen designed to house this stiffening rod or can be imbedded in the wall of the central tube 50. Upon insertion into the patient with the aid of an endoscope, when the central tube 50 reaches the location of the sharp bends in the duodenum 10, the stiffening rod 110 can be withdrawn, thereby allowing the central tube 50 to assume a pre-formed shape. In another embodiment, the central tube 50 may have a shape memory alloy wire embedded inside the central tube wall 51 or residing in the inner lumen 59. This shape memory alloy wire has a pre-set bend configuration with a radius β and a radius a that matches the bend configuration of the duodenum and is positioned in the central tube 50 at the corresponding location. Upon insertion into the patient with the aid of an endoscope, when the central tube 50 reaches the location of the sharp bend in the duodenum 10 and the shape memory alloy wire reaches a pre-set transition temperature equal to body temperature or about 37° C., the wire assumes the programmed shape and forces the central tube 50 and the central tube wall 51 to assume the same shape. In another embodiment, the central tube 50 may have a spring embedded inside the central tube wall 51 or inner lumen 59. This spring could be pre-shaped to the anatomy of the wall of the small intestine. The spring is held straight during delivery and conforms to the small intestine anatomy after release. The shape enables the device to remain in place. In one embodiment, due to its configuration that matches the predictable placement and configuration of the small intestine, the device can remain in place for a period of time within the small intestine without anchoring to the stomach or pylorus of the stomach. While the present embodiments of the present invention can remain in the small intestine for a period of time without anchoring to the stomach or pylorus, they are not intended to remain indefinitely. In one embodiment, the inserts are endoscopically removed after a predetermined period of time. In another embodiment, the inserts can be formed of a biodegradable material that is eventually degraded and eliminated from the body.

Figure 10:
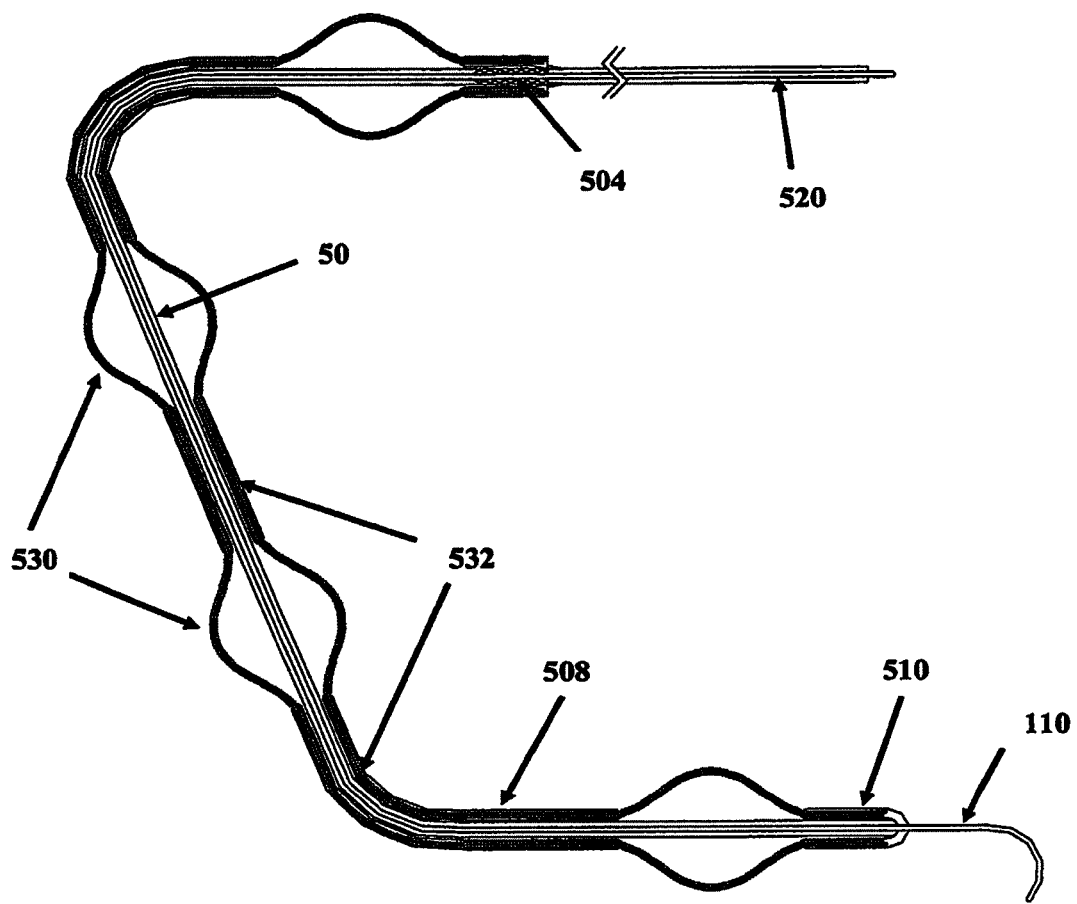
FIG. 10 illustrates a central tube attached to an expandable sleeve, the expandable sleeve allowing expansion of particular segments of the central tube to form flow reduction elements.

FIG. 10 illustrates an embodiment of the present invention where flow reduction elements can be created through the expansion of portions of an expandable sleeve. In the embodiment depicted in FIG. 10, a central tube 50 is attached to an expandable sleeve 508 at the expandable sleeve's distal end 510 near the distal portion of a duodenal/small intestinal insert of the present invention. In a delivery configuration of the depicted embodiment, the opposite proximal end of the central tube 50 is attached to a detachable extension tube 520 that can lock onto a proximal portion of the central tube 50 when the flow reduction elements 530 are expanded (post delivery). One non-limiting method of detachable attachment is the use of one or more screws 504, whereby the extension tube 520 screws into the central tube 50. The central tube 50 may be pre-formed to have a configuration that conforms to the anatomy of the duodenum 10 shown in FIG. 1. A central tube 50 so described would force the expandable sleeve 508 to assume the configuration of the central tube 50. The central tube 50 may be constructed of, without limitation, wire, spring, superelastic or shape memory alloys, hollow steel tubing or plastic polymers. In one embodiment a stiffening rod or guide wire 110 can also be inserted through the lumen of central tube 50. The expandable sleeve 508 may be, without limitation, one or more of a knit, a weave, a mesh or a braid that can be formed from, without limitation, one or more of a metal, a wire, a ribbon, a plastic polymer or a biodegradable material.

The expandable sleeve 508 herein described is designed to expand at predefined segments to allow the formation of flow reduction elements 530. In one embodiment, the non-expanded segments 532 of expandable sleeve 508 may be coated with a polymer to prevent their expansion. In another embodiment, the flow reduction elements 530 may be covered with a flexible polymer to prevent partially digested food from entering the flow reduction elements 530. In another embodiment, a stiffening rod or guide wire 110 can be inserted through the lumen of central tube 50 to straighten the central tube 50 when the device is delivered into the duodenum.

Figure 11:
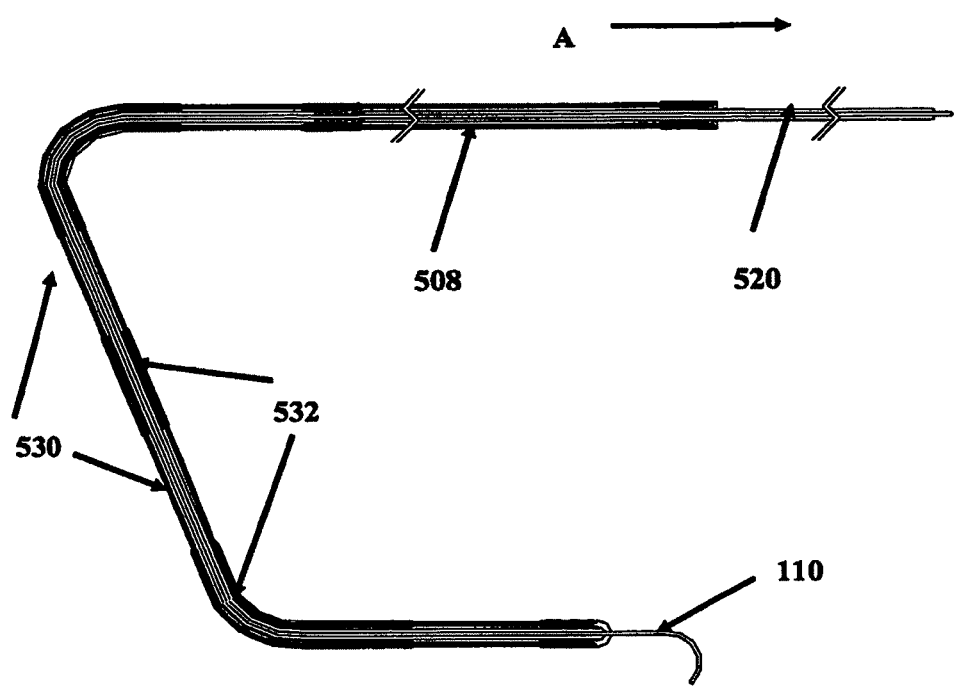
FIG. 11 illustrates an expandable sleeve in a collapsed configuration for insertion into the small intestine.

FIG. 11 illustrates the expandable sleeve 508 consisting of flow reduction elements 530 in a collapsed configuration for insertion into the small intestine. In this configuration a force A is applied to the expandable sleeve 508 to collapse the flow reduction elements 530. The collapsed form can be restrained by a constraining mechanism such as, without limitation, a sheath or a tightly wound string, or by applying sustained traction on the proximal end of the expandable sleeve 508. FIG. 11 also shows portions of the central tube that will remain unexpanded 532, a detachable extension tube 520 and a guidewire 110.

The expansion of the flow reduction elements 530 in the embodiments depicted in FIGS. 10 and 11 can occur passively or actively. One non-limiting example of passive expansion can be the removal of a constraining mechanism to allow the flow reduction elements 530 to expand to an original expanded state. Another non-limiting mechanism can be to release traction on the proximal end of an expandable sleeve 508 to allow the flow reduction elements 530 to expand to an original expanded state.

The flow reduction elements 530 of the embodiments depicted in FIGS. 10 and 11 can expand in a distal to proximal fashion, a proximal to distal fashion or in a central fashion depending on their relative position in relation to, in one embodiment, motion of the expandable sleeve 508 and the central tube 50 to one another. For example, if the proximal end of the flow reduction element lumen is held in the duodenal bulb and the central tube 50 is pulled back, the distal end of the flow reduction element lumen can expand first. Expansion in this direction can be advantageous because the position of the proximal end of the flow reduction element lumen remains in the duodenal bulb.

Figure 12:
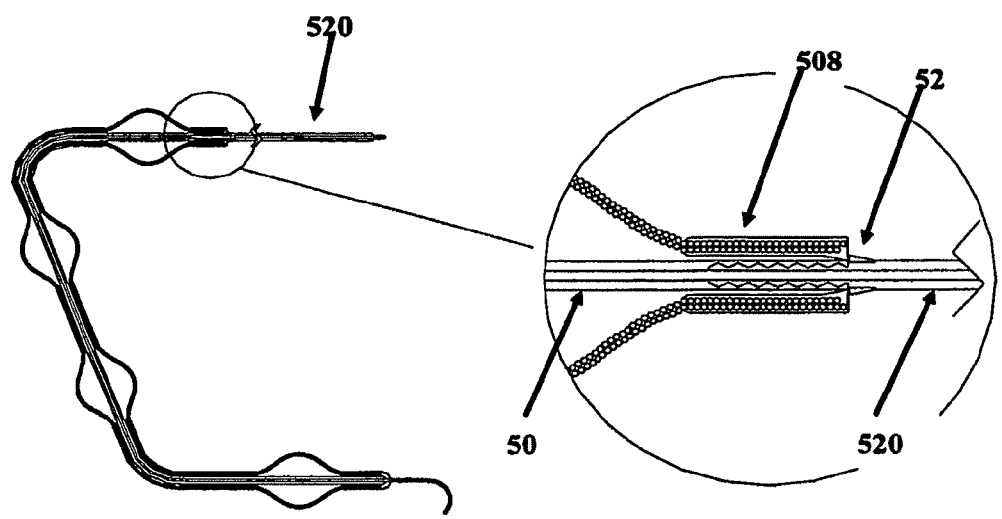
FIG. 12 illustrates one mechanism for keeping flow reduction elements formed with an expandable sleeve in a desired expanded configuration.

FIG. 12 illustrates one embodiment of the present invention that can lock the proximal end of the expandable sleeve 508 to the central tube 50 at a position to keep the flow reduction elements in a desired expanded configuration. Traction on the extension tube 520 retracts central tube 50 until wedge 52 engages the proximal end of the expandable sleeve 508. The central tube 50 may have multiple ratchet-like wedges that can lock the expandable sleeve 508 at different degrees of expansion. The extension tube can be unscrewed from the central tube 50 after deployment of the device and expansion of the expandable sleeve 508.

As previously stated, in one embodiment, the central tube and/or flow reduction elements of the present invention can be adapted to release bioactive materials or other signals that trigger biological satiety signals. In one embodiment, the one or more of the flow reduction elements and/or central tube may be a porous and malleable solid designed to release a signal into the GI tract over time. In one embodiment, nutrient products of digestion are released from the one or more flow reduction elements and/or central tube to trigger chemoreceptors within the GI tract to release molecular signals involved in transmitting and/or creating satiety signals.

In addition to delivering bioactive materials to the small intestine that can reduce food intake, the methods and devices of the present invention can be used to deliver other bioactive materials normally taken orally as well. The release of bioactive materials directly into the small intestine can be advantageous because many bioactive materials, including many drugs that are generally taken orally, are degraded by the harsh conditions of the stomach before they can reach the small intestine to be absorbed. For this reason, many bioactive materials are coated with layers of protective materials. By releasing bioactive materials, including drugs, directly into the small intestine, coatings to protect the bioactive materials are not required. This lack of required protective coatings can be beneficial for patients because less unnecessary substances are introduced into their systems. It also is beneficial to bioactive material and drug manufacturers as a cost reduction measure.

The central tube and/or flow reduction elements of the present invention can have bioactive materials adhered to their surface (through dip-coating, spray-coating, sputter-coating and a variety of other techniques known to those of skill in the art) or can be manufactured so that the materials making up the intestinal insert include and diffuse such bioactive materials. The central tube and/or flow reduction elements of the present invention that diffuse bioactive materials, can be created by a number of different procedures. For example, U.S. Pat. No. 5,019,400 to Gombotz et al., which is hereby incorporated by reference, describes a low temperature casting process for incorporating proteins into controlled release polymer matrices. U.S. Pat. No. 6,685,957 to Bezemer et al., which is hereby incorporated by reference, describes a method to create a fibrous polymer loaded with bioactive materials that is suitable for loading bioactive materials such as by-products of digestion. In one embodiment, the methods described in U.S. Pat. No. 6,685,957 include synthesizing a polyethylene glycol terephtalate/polybutylene terephthalate copolymer from a mixture of dimethyl terephthalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene and/or the polyethyene glycol. After transesterification, the temperature is raised slowly to about 245° C., and a vacuum (finally less than 0.1 mbar) is achieved. The excess butanediol is distilled off and a prepolymer of butanediol terephthalate condenses with the polyethylene glycol to form a polyethylene/polybutylene terephthalate copolymer. A terephthalate moiety connects the polyethylene glycol units to the polybutylene terephthalate units of the copolymer and thus such a copolymer also is sometimes referred to as a polyethylene glycol terephtalate/polybutylene terephthalate copolymer (PEGT/PBT copolymer).

When a hydrophobic bioactive material, such as, for example, a steroid hormone is incorporated by the above-described method, at least one hydrophobic antioxidant can be present. Hydrophobic antioxidants which may be employed include, but are not limited to, tocopherols (such as, without limitation, α-tocopherol, β-tocopherol, γ-tocopherol, Δ-tocopherol, ε-tocopherol, $\zeta_1$-tocopherol, $\zeta_2$-tocopherol, and η-tocopherol) and 1-ascorbic acid 6-palmitate. Such hydrophobic antioxidants retard the degradation of the copolymer and retard the release of the bioactive material. Thus, the use of a hydrophobic or lipophilic antioxidant is applicable particularly to the formation of loaded polymers which include bioactive materials which tend to be released quickly, such as, for example, bioactive materials having a molecular weight less than 500. The hydrophobic antioxidant(s) may be present in the loaded polymer in an amount of from about 0.1 wt % to about 10 wt % of the total weight of the polymer, or from about 0.5 wt % to about 2 wt %.

When a loaded polymer made according to the above-described technique includes a hydrophilic bioactive material, the loaded polymer may also include, in addition to a hydrophobic antioxidant, a hydrophobic molecule such as, without limitation, cholesterol, ergosterol, lithocholic acid, cholic acid, dinosterol, betuline, or oleanolic acid, which may be employed in order to retard the release rate of the agent from the copolymer. Such hydrophobic molecules prevent water penetration into the loaded polymer, but do not compromise the degradability of the polymer matrix. In addition, such molecules have melting points from about 150° C. to about 200° C. and/or decrease the polymer matrix diffusion coefficient for the bioactive material to be released. Thus, such hydrophobic molecules provide for a more sustained release of a bioactive material from the polymer matrix. The at least one hydrophobic molecule may be present in the loaded polymer in an amount of from about 0.1 wt % to about 20 wt %, or from 1.0 wt % to 5.0 wt %.

U.S. Pat. No. 6,187,330 to Wang et al., which is hereby expressly incorporated by reference, describes a method of dispersing bioactive materials, including peptides and proteins, into a polymer by dispersing the bioactive material in a glassy matrix phase during the melt stage of the polymer wherein the glass transition temperature is higher than the melting point of the polymer. The glassy matrix phase described in U.S. Pat. No. 6,187,330 can be produced by lyophilizing an aqueous solution of the bioactive material and an appropriate thermoprotectant (such as, without limitation, trehalose, melezitose, lactose, maltose, cellobiose, melibiose and raffinose). The particular thermoprotectant selected and its concentration relative to the bioactive material determines the precise glass transition temperature of the lyophile. Generally, the weight ratio of thermoprotectant to bioactive material is between about 2 and 200. One skilled in the art can determine the required glass transition temperature of any combination. Glass transition is defined as the reversible change in an amorphous material from (or to) a viscous rubbery state to (or from) a hard and relatively brittle one (American Society for Testing and Materials (ASTM) E 1142). Glass transition temperature (Tg) is defined as the approximate midpoint of the temperature range at which the glass transition takes place (ASTM D 4092). The glass transition temperature of the glassy matrix phase containing the peptide bioactive material and the thermoprotectant can be determined by a variety of techniques, the most popular of which is differential scanning calorimetry (DSC). If a glassy material is heated at a constant rate, a baseline shift can be found in the relation of heat flow and its temperature. The temperature corresponding to the midpoint of the two baselines is considered the glass transition temperature.

Lyophilization of the aqueous solution containing the thermoprotectant, bioactive material and other appropriate excipients, if any, is carried out using techniques well known in the pharmaceutical field (see, e.g., REMINGTON'S PHARMACEUTICAL SCIENCES, 17$^{th}$ Ed., p. 1538). Lyophilization produces a glassy matrix phase in the form of a powder or a cake which may be comminuted to produce a powder suitable for dispersion in the polymer.

Non-limiting examples of polymers that can be used in accordance with the present invention include polyurethanes, polyesterurethanes, silicone, fluoropolymers, ethylene vinyl acetate, polyethylene, polypropylene, polycarbonates, trimethylenecarbonate, polyphosphazene, polyhydroxybutyrate, polyhydroxyvalerate, polydioxanone, polyiminocarbonates, polyorthoesters, ethylene vinyl alcohol copolymer, L-polylactide, D,L-polylactide, polyglycolide, polycaprolactone, copolymers of lactide and glycolide, polymethylmethacrylate, poly(n-butyl)methacrylate, polyacrylates, polymethacrylates, elastomers, and mixtures thereof. Representative elastomers that can also be used include, without limitation, a thermoplastic elastomer material available under the trade name "C-FLEX" from Concept Polymer Technologies of Largo, Fla., polyether-amide thermoplastic elastomer, fluoroelastomers, fluorosilicone elastomer, sytrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, polyester, styrene, ethylene, propylene, butadiene and isoprene, polyester thermoplastic elastomer, and mixtures thereof.

One of skill in the art can determine the amount or concentration of bioactive material(s) to include on the surface or within the material of the intestinal inserts of the present invention depending on particular treatment objectives and desired release profiles. Factors to consider are described in, for example, U.S. Pat. No. 6,939,557 to Rowe et al. (which is hereby expressly incorporated by reference) and include the hydrophobic or hydrophilic nature of the bioactive material(s), the aggregation and solubility characteristics of the bioactive material(s) and their particle size; see also REMINGTON: THE SCIENCE AND PRACTICE OF PHARMACY, 20$^{th}$ ed. Ch. 47, Controlled Release Drug Delivery Systems, which is hereby expressly incorporated by reference.

In one embodiment, the intestinal inserts of the present invention, or portions thereof, can include a topcoat or barrier to slow the diffusion or release of bioactive materials. Typically, the barrier should be biocompatible (i.e., its presence does not elicit an adverse response from the body), and can have a thickness ranging from about 50 angstroms to about 20,000 angstroms. In one embodiment the barrier may include a polymer provided over the polymer that diffuses bioactive materials.

In another embodiment, a barrier of the present invention comprises inorganic materials. Appropriate inorganic materials include, without limitation, silicides, oxides, nitrides, and carbides. Suitable silicides may include, without limitation, silicides of vanadium, zirconium, tungsten, titanium, niobium, and tantalum. Suitable oxides may include, without limitation, oxides of aluminum, barium, calcium, hafnium, niobium, silicon, tantalum, titanium, tungsten, and zirconium. Suitable nitrides may include, without limitation, nitrides of chromium, silicon, titanium, and zirconium. Suitable carbides may include, without limitation, carbides of silicon and titanium. Other suitable materials may include, without limitation, molybdenum disulfide, amorphous diamond, diamond-like carbon, pyrolytic carbon, ultra-low temperature isotropic (ULTI) carbon, amorphous carbon, strontium titanate, and barium titanate. Also suitable for use are pure metals, such as, without limitation, aluminum, chromium, gold, hafnium, iridium, niobium, palladium, platinum, tantalum, titanium, tungsten, zirconium, and alloys of these metals.

Several methods may be used to deposit a barrier over the inserts of the present invention. For example, silicide compounds, such as, without limitation, vanadium disilicide, zirconium disilicide, tungsten disilicide, titanium disilicide, niobium disilicide, tantalum disilicide, vanadium silicide, titanium trisilicide, and tantalum trisilicide may be deposited by sputtering or chemical vapor deposition (CVD). Oxide barrier coatings, such as, without limitation, tantalum oxide, titanium dioxide, zirconium oxide, niobium oxide, tungsten oxide, aluminum oxide, and silicon dioxide can be produced by reactive sputtering. The power source used in this method may be AC or DC, and utilizes the pure element as a target with a sputter gas of argon and low levels of oxygen.

Nitride barrier coatings, such as, without limitation, titanium nitride, titanium carbonitride, chromium nitride, titanium aluminum nitride, and zirconium nitride can be deposited on the inserts of the present invention at relatively low temperatures (i.e., less than 60° C.) by cathodic arc vacuum deposition. Such a method may be chosen where bioactive materials included within an insert of the present invention are temperature-sensitive.

Films of pure metals (without limitation, aluminum, gold, tungsten and platinum) may be produced by methods such as, without limitation, physical vapor deposition (PVD), sputtering, thermal evaporation, or electron beam evaporation. Alloys of these metals can be deposited by sputtering if, for example, an alloy sputtering target is used or multiple targets are simultaneously sputtered. Alloys may also be deposited utilizing thermal evaporation or electron beam evaporation if several evaporation sources are used simultaneously.

In one embodiment, it is contemplated that the bather will contain mostly inorganic material. However, other embodiments can include bathers with a mixture of organic and inorganic materials or bathers of all organic materials. Some organic compounds that can be used in accordance with the present invention include, without limitation, polyacrylonitrile, polyvinylidene chloride, nylon 6-6, perfluoropolymers, polyethylene terephthalate, polyethylene 2,6-napthalene dicarboxylate, and polycarbonate. Generally, the solubility of the drug in the material of the barrier is less than the solubility of the drug in its polymer carrier. Also, generally, the diffusivity of the drug in the material of the bather is lower than the diffusivity of the drug in its polymer carrier. The bather may or may not be biodegradable.

Appropriate biodegradable materials that may be used to create a bather include, without limitation, calcium phosphates such as, without limitation, hydroxyapatite, carbonated hydroxyapatite, tricalcium phosphate, beta-tricalcium phosphate, octacalcium phosphate, amorphous calcium phosphate, and calcium orthophosphate. Certain calcium salts such as calcium phosphate (plaster of paris) may also be used. The biodegradability of the bather may act as an additional mechanism for controlling drug release from the underlying first layer.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention can be combined with any one or more other features of any other embodiment of the invention, without departing from the scope of the invention.

What is claimed is:

1. A device adapted and configured for use within a duodenum of a mammal, comprising:
   a spine having a length, a proximal end, and a distal end;
   an anchor positioned adjacent to the spine proximal end, wherein the length of the spine is selected so that when the anchor is in the stomach, the distal end of the spine is in the duodenum; and
   a flow reduction element positioned along the spine such that when the anchor is in the stomach, the flow reduction element is in the duodenum, wherein the flow reduction element is configured to self-expand from a collapsed delivery configuration to an expanded configuration in the duodenum
   wherein the flow reduction element in the expanded configuration is configured to slow a flow of partially-digested food through the duodenum, the flow reduction element in the expanded configuration having a proximal end, a distal end, a hollow interior portion bounded by an interior wall, and an exterior portion bounded by an exterior wall, wherein at least a portion of the flow reduction element is coated with a lipophilic material or is made of a material having a lipophilic material therein.

2. The device of claim 1, wherein the spine is hollow.

3. The device of claim 1, further comprising a feature on the spine positioned to restrict movement of the flow reduction element relative to the spine.

4. The device of claim 1, wherein there are a plurality of flow reduction elements positioned along the spine.

5. The device of claim 1, wherein the flow reduction element is a sphere.

6. The device of claim 1, wherein the flow reduction element is an ovoid.

7. The device of claim 1, wherein the flow reduction element has an elliptical shape.

8. The device of claim 1, wherein the flow reduction element has an irregular non-geometrical shape.

9. The device of claim 1, wherein the flow reduction element is eccentrically attached to the spine.

10. The device of claim 1, wherein the flow reduction element is concentrically attached to the spine.

11. The device of claim 1, wherein the spine is solid.

12. The device of claim 1, wherein the spine is pre-formed with a configuration that conforms to angulations of the duodenum and returns to the preformed configuration when in place in the gastrointestinal tract.

13. The device of claim 1, wherein the flow reduction element is part of an expandable sleeve placed around the spine.

14. The device of claim 1, wherein the walls of the flow reduction element are mesh.

15. The device of claim 1, wherein at least a portion of the device is made of a material having a lipophilic material therein, and wherein the lipophilic material is diffused within the material of the device.

16. The device of claim 1, wherein the flow reduction element is attached to the spine.

17. The device of claim 1, wherein the flow reduction element is configured to increase exposure of partially-digested food to walls of the duodenum.

18. The device of claim 1, wherein the flow reduction element in the expanded configuration has a diameter about equivalent to a diameter of the duodenum.

* * * * *